US006805868B1

(12) United States Patent
Thonnard

(10) Patent No.: US 6,805,868 B1

(45) Date of Patent: Oct. 19, 2004

(54) MORAXELLA CATARRHALIS ANTIGEN, CORRESPONDING GENE AND USES THEREOF

(75) Inventor: Joelle Thonnard, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 10/088,045

(22) PCT Filed: Sep. 14, 2000

(86) PCT No.: PCT/EP00/09035

§ 371 (c)(1), (2), (4) Date: Jun. 7, 2002

(87) PCT Pub. No.: WO01/19996

PCT Pub. Date: Mar. 22, 2001

(30) Foreign Application Priority Data

Sep. 14, 1999 (EP) ............................................. 9921691

(51) Int. Cl.[7] .......................... A61K 39/02; C12N 1/20; C12N 15/09; C12P 21/06

(52) U.S. Cl. ................................ 424/251.1; 424/234.1; 424/200.1; 424/192.1; 424/190.1; 424/185.1; 435/69.7; 435/69.3; 536/23.1; 536/23.4; 536/24.3; 530/300; 530/350

(58) Field of Search ........................... 424/251.1, 234.1, 424/200.1, 192.1, 190.1, 185.1, 69.1; 435/69.7, 69.3; 530/300, 350; 536/23.1, 23.4, 24.3, 23.6, 26.3

(56) References Cited

U.S. PATENT DOCUMENTS 5,712,118 A 1/1998 Murphy

FOREIGN PATENT DOCUMENTS

| | | |
|---|---|---|
| WO | WO 93/03761 | 3/1993 |
| WO | WO 97/41731 | 11/1997 |
| WO | WO 98/33814 | 8/1998 |

OTHER PUBLICATIONS

Hoehn et al (Infection and Immunity 1992, 60; 4695–4703 (1992), and Accession No.: Q02219.*

Helminen et al 1994 (J. Infec. Dis, 170; 867–872).*

Jobling et al. (Mol. Microbiol. 1991, 5(7): 1755–67.*

Lazar et al., Molecular and Cellular Biology, 8(3): 1247–1252, 1988.*

Burgess et al., The Journal of Cell Biology, 111:2129–2138, 1990.*

Rudinger et al, in “Peptide Hormones”, edited by Parsons, J.A., University Park Press, Jun. 1976, p. 6.*

* cited by examiner

*Primary Examiner*—Mark Navarro
*Assistant Examiner*—Padma Baskar
(74) *Attorney, Agent, or Firm*—Jeffrey A. Sutton; Eric A. Meade

(57) ABSTRACT

The invention provides BASB109 polypeptides and polynucleotides encoding BASB109 polypeptides and methods for producing such polypeptides by recombinant techniques. Also provided are diagnostic, prophylactic and therapeutic uses.

13 Claims, 13 Drawing Sheets

Figure 1A

Identity to SeqID No:1 is indicated by a dot. Gap is indicated by a dash.

```
*         20           *
Seqid1 : ATGTCTAAGCCTACTTTGATAAAAACAACC :  30
Seqid3 : .............................. :  30

                  40           *          60
Seqid1 : TTAATTTGTGCCTTAAGTGCATTGATGCTC :  60
Seqid3 : .............................. :  60

                   *          80          *
Seqid1 : AGTGGTTGTAGCAATCAAGCGGACAAAGCC :  90
Seqid3 : .............................. :  90

                 100           *         120
Seqid1 : GCCCAGCCAAAAAGCAGCACGGTAGACGCT : 120
Seqid3 : .............................. : 120

                   *         140          *
Seqid1 : GCCGCCAAGACAGCAAATGCAGATAATGCT : 150
Seqid3 : .............................. : 150

                 160           *         180
Seqid1 : GCCTCACAAGAACATCAAGGCGAGCTGCCT : 180
Seqid3 : .............................. : 180
```

Figure 1B

```
                 *         200          *
Seqid1 : GTCATTGATGCCATTGTTACGCATGCACCA :  210
Seqid3 : ..............................  :  210

               220          *         240
Seqid1 : GAAGTTCCACCACCTGTTGACCGTGACCAC :  240
Seqid3 : ..............................  :  240

                 *         260          *
Seqid1 : CCCGCCAAAGTGGTGGTAAAAATGGAAACC :  270
Seqid3 : ..............................  :  270

               280          *         300
Seqid1 : GTTGAAAAAGTCATGCGTCTGGCAGATGGC :  300
Seqid3 : ..............................  :  300

                 *         320          *
Seqid1 : GTGGAATATCAGTTTTGGACATTTGGCGGT :  330
Seqid3 : ..............................  :  330

               340          *         360
Seqid1 : CAAGTTCCAGGGCAGATGATTCGTGTGCGT :  360
Seqid3 : ..............................  :  360

                 *         380          *
Seqid1 : GAAGGCGACACCATCGAAGTGCAGTTCTCA :  390
Seqid3 : ..............................  :  390
```

Figure 1C

```
                   400          *         420
Seqid1 : AACCACCCAGATTCAAAAATGCCCCATAAT :  420
Seqid3 : .............................. :  420

                     *         440         *
Seqid1 : GTTGACTTTCACGCTGCCACAGGGCCTGGC :  450
Seqid3 : .............................. :  450

                   460          *         480
Seqid1 : GGCGGGGCAGAAGCGTCATTTACCGCACCG :  480
Seqid3 : .............................. :  480

                     *         500         *
Seqid1 : GGTCATACATCAACCTTTAGTTTTAAAGCC :  510
Seqid3 : .............................. :  510

                   520          *         540
Seqid1 : TTACAGCCTGGTTTGTATGTCTATCACTGT :  540
Seqid3 : .............................. :  540

                     *         560         *
Seqid1 : GCGGTTGCCCCTGTTGGCATGCACATTGCT :  570
Seqid3 : .............................. :  570

                   580          *         600
Seqid1 : AATGGCATGTATGGTTTGATTTTGGTTGAA :  600
Seqid3 : .............................. :  600
```

Figure 1D

```
                      *        620          *
Seqid1 : CCAAAAGAGGGCTTGCCAAAAGTAGATAAA : 630
Seqid3 : .............................. : 630

                     640          *        660
Seqid1 : GAATACTATGTCATGCAAGGCGACTTTTAT : 660
Seqid3 : .............................. : 660

                      *        680          *
Seqid1 : ACCAAAGGCAAATATGGCGAACAAGGTCTA : 690
Seqid3 : .............................. : 690

                     700          *        720
Seqid1 : CAGCCCTTTGATATGGAAAAAGCCATTCGA : 720
Seqid3 : .............................. : 720

                      *        740          *
Seqid1 : GAAGATGCTGAATATGTTGTCTTTAATGGT : 750
Seqid3 : .............................. : 750

                     760          *        780
Seqid1 : TCGGTGGGGGCGTTGACTGGTGAAAATGCT : 780
Seqid3 : .............................. : 780

                      *        800          *
Seqid1 : CTAAAAGCCAAGGTTGGCGAAACTGTTCGC : 810
Seqid3 : .............................. : 810
```

Figure 1E

```
                820          *         840
Seqid1  :  TTATTTGTGGGTAACGGCGGCCCGAATTTG  :   840
Seqid3  :  ..............................  :   840

                 *         860         *
Seqid1  :  ACATCATCATTCCATGTCATTGGTGAGATT  :   870
Seqid3  :  ..............................  :   870

                880          *         900
Seqid1  :  TTTGATAAGGTTCACTTTGAGGGTGGTAAG  :   900
Seqid3  :  ..............................  :   900

                 *         920         *
Seqid1  :  GGTGAAAACCACAATATCCAAACCACGCTA  :   930
Seqid3  :  ..............................  :   930

                940          *         960
Seqid1  :  ATCCCAGCAGGTGGCGCTGCCATCACTGAA  :   960
Seqid3  :  ..............................  :   960

                 *         980         *
Seqid1  :  TTTAAGGTGGATGTGCCGGGTGATTATGTC  :   990
Seqid3  :  ..............................  :   990

               1000          *        1020
Seqid1  :  TTGGTTGACCATGCCATCTTCCGTGCCTTT  :  1020
Seqid3  :  ..............................  :  1020
```

Figure 1F

```
               *        1040         *
Seqid1 : AACAAAGGGGCATTGGGCATACTTAAGGTG : 1050
Seqid3 : .............................. : 1050

            1060         *        1080
Seqid1 : GAAGGTGAAGAAAATCATGAGATTTATTCA : 1080
Seqid3 : .............................. : 1080

               *        1100         *
Seqid1 : CACAAACAAACAGACGCTGTCTATCTGCCA : 1110
Seqid3 : .............................. : 1110

            1120         *        1140
Seqid1 : GAGGGTGCCCCACAAGCAATTGATACCCAA : 1140
Seqid3 : .............................. : 1140

               *        1160         *
Seqid1 : GAAGCACCCAAAACACCTGCACCTGCCAAC : 1170
Seqid3 : .............................. : 1170

            1180         *        1200
Seqid1 : TTACAAGAGCAGATTAAAGCAGGTAAGGCA : 1200
Seqid3 : .............................. : 1200

               *        1220         *
Seqid1 : ACCTATGACTCTAACTGTGCTGCTTGTCAC : 1230
Seqid3 : .............................. : 1230
```

Figure 1G

```
                 1240         *         1260
Seqid1 : CAACCTGATGGTAAAGGCGTGCCAAACGCT : 1260
Seqid3 : .............................. : 1260

                    *       1280         *
Seqid1 : TTCCCACCGCTTGCCAACTCTGACTATCTG : 1290
Seqid3 : .............................. : 1290

                 1300         *         1320
Seqid1 : AACGCCGACCACGCTCGTGCCGCCAGCATC : 1320
Seqid3 : .............................. : 1320

                    *       1340         *
Seqid1 : GTGGCAAATGGATTGTCTGGTAAGATTACC : 1350
Seqid3 : .............................. : 1350

                 1360         *         1380
Seqid1 : GTCAATGGCAACCAATATGAAAGCGTCATG : 1380
Seqid3 : .............................. : 1380

                    *       1400         *
Seqid1 : CCTGCGATTGCTCTGAGCGACCAACAGATT : 1410
Seqid3 : .............................. : 1410
```

Figure 1H

```
                 1420          *        1440
Seqid1 : GCCAATGTCATCACCTACACGCTTAACAGC : 1440
Seqid3 : .............................. : 1440

                   *        1460          *
Seqid1 : TTTGGTAACAAAGGCGGTCAACTCAGTGCA : 1470
Seqid3 : .............................. : 1470

                 1480          *        1500
Seqid1 : GACGATGTGGCAAAAGCCAAAAAAACCAAG : 1500
Seqid3 : .............................. : 1500

Seqid1 : CCAAACTGA : 1509
Seqid3 : ......--- : 1506
```

Figure 2A

Identity to SeqID No:2 is indicated by a dot. Gap is indicated by a dash.

```
Seqid2 : MSKPTLIKTTLICALSALMLSGCSNQADKA :  30
Seqid4 : .............................. :  30

                 40         *         60
Seqid2 : AQPKSSTVDAAAKTANADNAASQEHQGELP :  60
Seqid4 : .............................. :  60

                  *        80         *
Seqid2 : VIDAIVTHAPEVPPPVDRDHPAKVVVKMET :  90
Seqid4 : .............................. :  90

                100         *        120
Seqid2 : VEKVMRLADGVEYQFWTFGGQVPGQMIRVR : 120
Seqid4 : .............................. : 120

                  *       140         *
Seqid2 : EGDTIEVQFSNHPDSKMPHNVDFHAATGPG : 150
Seqid4 : .............................. : 150

                160         *        180
Seqid2 : GGAEASFTAPGHTSTFSFKALQPGLYVYHC : 180
```

Figure 2B

```
Seqid4 : .............................. : 180

                    *          200           *
Seqid2 : AVAPVGMHIANGMYGLILVEPKEGLPKVDK : 210
Seqid4 : .............................. : 210

             220            *          240
Seqid2 : EYYVMQGDFYTKGKYGEQGLQPFDMEKAIR : 240
Seqid4 : .............................. : 240

                    *          260           *
Seqid2 : EDAEYVVFNGSVGALTGENALKAKVGETVR : 270
Seqid4 : .............................. : 270

             280            *          300
Seqid2 : LFVGNGGPNLTSSFHVIGEIFDKVHFEGGK : 300
Seqid4 : .............................. : 300

                    *          320           *
Seqid2 : GENHNIQTTLIPAGGAAITEFKVDVPGDYV : 330
Seqid4 : .............................. : 330
```

Figure 2C

```
                  340         *        360
Seqid2 : LVDHAIFRAFNKGALGILKVEGEENHEIYS : 360
Seqid4 : .............................. : 360

                    *        380         *
Seqid2 : HKQTDAVYLPEGAPQAIDTQEAPKTPAPAN : 390
Seqid4 : .............................. : 390

                  400         *        420
Seqid2 : LQEQIKAGKATYDSNCAACHQPDGKGVPNA : 420
Seqid4 : .............................. : 420

                    *        440         *
Seqid2 : FPPLANSDYLNADHARAASIVANGLSGKIT : 450
Seqid4 : .............................. : 450

                  460         *        480
Seqid2 : VNGNQYESVMPAIALSDQQIANVITYTLNS : 480
Seqid4 : .............................. : 480
```

Figure 2D

```
                    *         500
Seqid2 : FGNKGGQLSADDVAKAKKTKPN : 502
Seqid4 : ...................... : 502
```

Figure 3-A
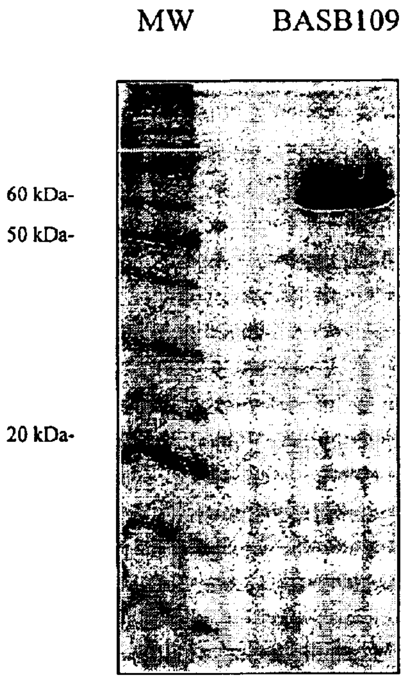
Fig. 3-B
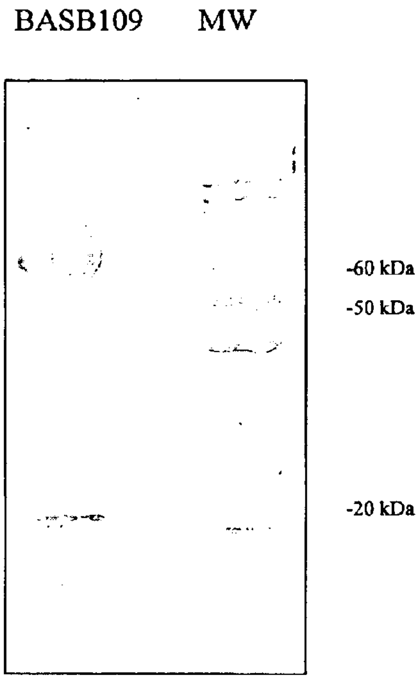

SEQUENCE LISTING

<160> NUMBER OF SEQ ID NOS: 10

<210> SEQ ID NO 1
<211> LENGTH: 1509
<212> TYPE: DNA
<213> ORGANISM: Moraxella catarrhalis

<400> SEQUENCE: 1

-continued

```
atgtctaagc ctactttgat aaaaacaacc ttaatttgtg ccttaagtgc attgatgctc     60

agtggttgta gcaatcaagc ggacaaagcc gcccagccaa aaagcagcac ggtagacgct    120

gccgccaaga cagcaaatgc agataatgct gcctcacaag aacatcaagg cgagctgcct    180

gtcattgatg ccattgttac gcatgcacca gaagttccac cacctgttga ccgtgaccac    240

cccgccaaag tggtggtaaa aatggaaacc gttgaaaaag tcatgcgtct ggcagatggc    300

gtggaatatc agttttggac atttggcggt caagttccag ggcagatgat tcgtgtgcgt    360

gaaggcgaca ccatcgaagt gcagttctca aaccacccag attcaaaaat gccccataat    420

gttgactttc acgctgccac agggcctggc ggcggggcag aagcgtcatt taccgcaccg    480

ggtcatacat caacctttag ttttaaagcc ttacagcctg gtttgtatgt ctatcactgt    540

gcggttgccc ctgttggcat gcacattgct aatggcatgt atggtttgat tttggttgaa    600

ccaaaagagg gcttgccaaa agtagataaa gaatactatg tcatgcaagg cgacttttat    660

accaaaggca aatatggcga acaaggtcta cagccctttg atatggaaaa agccattcga    720

gaagatgctg aatatgttgt ctttaatggt tcggtggggg cgttgactgg tgaaaatgct    780

ctaaaagcca aggttggcga aactgttcgc ttatttgtgg gtaacggcgg cccgaatttg    840

acatcatcat tccatgtcat tggtgagatt tttgataagg ttcactttga gggtggtaag    900

ggtgaaaacc acaatatcca aaccacgcta atcccagcag gtggcgctgc catcactgaa    960

tttaaggtgg atgtgccggg tgattatgtc ttggttgacc atgccatctt ccgtgccttt   1020

aacaaagggg cattgggcat acttaaggtg gaaggtgaag aaaatcatga gatttattca   1080

cacaaacaaa cagacgctgt ctatctgcca gagggtgccc cacaagcaat tgatacccaa   1140

gaagcaccca aaacacctgc acctgccaac ttacaagagc agattaaagc aggtaaggca   1200

acctatgact ctaactgtgc tgcttgtcac caacctgatg gtaaaggcgt gccaaacgct   1260

ttcccaccgc ttgccaactc tgactatctg aacgccgacc acgctcgtgc cgccagcatc   1320

gtggcaaatg gattgtctgg taagattacc gtcaatggca accaatatga aagcgtcatg   1380

cctgcgattg ctctgagcga ccaacagatt gccaatgtca tcacctacac gcttaacagc   1440

tttggtaaca aaggcggtca actcagtgca gacgatgtgg caaaagccaa aaaaaccaag   1500

ccaaactga                                                            1509
```

<210> SEQ ID NO 2
<211> LENGTH: 502
<212> TYPE: PRT
<213> ORGANISM: Moraxella catarrhalis

<400> SEQUENCE: 2

```
Met Ser Lys Pro Thr Leu Ile Lys Thr Thr Leu Ile Cys Ala Leu Ser
 1               5                  10                  15

Ala Leu Met Leu Ser Gly Cys Ser Asn Gln Ala Asp Lys Ala Ala Gln
            20                  25                  30

Pro Lys Ser Ser Thr Val Asp Ala Ala Ala Lys Thr Ala Asn Ala Asp
        35                  40                  45

Asn Ala Ala Ser Gln Glu His Gln Gly Glu Leu Pro Val Ile Asp Ala
    50                  55                  60

Ile Val Thr His Ala Pro Glu Val Pro Pro Pro Val Asp Arg Asp His
65                  70                  75                  80

Pro Ala Lys Val Val Val Lys Met Glu Thr Val Glu Lys Val Met Arg
                85                  90                  95

Leu Ala Asp Gly Val Glu Tyr Gln Phe Trp Thr Phe Gly Gly Gln Val
```

-continued

```
            100                 105                 110

Pro Gly Gln Met Ile Arg Val Arg Glu Gly Asp Thr Ile Glu Val Gln
        115                 120                 125

Phe Ser Asn His Pro Asp Ser Lys Met Pro His Asn Val Asp Phe His
    130                 135                 140

Ala Ala Thr Gly Pro Gly Gly Gly Ala Glu Ala Ser Phe Thr Ala Pro
145                 150                 155                 160

Gly His Thr Ser Thr Phe Ser Phe Lys Ala Leu Gln Pro Gly Leu Tyr
                165                 170                 175

Val Tyr His Cys Ala Val Ala Pro Val Gly Met His Ile Ala Asn Gly
            180                 185                 190

Met Tyr Gly Leu Ile Leu Val Glu Pro Lys Glu Gly Leu Pro Lys Val
        195                 200                 205

Asp Lys Glu Tyr Tyr Val Met Gln Gly Asp Phe Tyr Thr Lys Gly Lys
    210                 215                 220

Tyr Gly Glu Gln Gly Leu Gln Pro Phe Asp Met Glu Lys Ala Ile Arg
225                 230                 235                 240

Glu Asp Ala Glu Tyr Val Val Phe Asn Gly Ser Val Gly Ala Leu Thr
                245                 250                 255

Gly Glu Asn Ala Leu Lys Ala Lys Val Gly Glu Thr Val Arg Leu Phe
            260                 265                 270

Val Gly Asn Gly Gly Pro Asn Leu Thr Ser Ser Phe His Val Ile Gly
        275                 280                 285

Glu Ile Phe Asp Lys Val His Phe Glu Gly Gly Lys Gly Glu Asn His
    290                 295                 300

Asn Ile Gln Thr Thr Leu Ile Pro Ala Gly Gly Ala Ala Ile Thr Glu
305                 310                 315                 320

Phe Lys Val Asp Val Pro Gly Asp Tyr Val Leu Val Asp His Ala Ile
                325                 330                 335

Phe Arg Ala Phe Asn Lys Gly Ala Leu Gly Ile Leu Lys Val Glu Gly
            340                 345                 350

Glu Glu Asn His Glu Ile Tyr Ser His Lys Gln Thr Asp Ala Val Tyr
        355                 360                 365

Leu Pro Glu Gly Ala Pro Gln Ala Ile Asp Thr Gln Glu Ala Pro Lys
    370                 375                 380

Thr Pro Ala Pro Ala Asn Leu Gln Glu Gln Ile Lys Ala Gly Lys Ala
385                 390                 395                 400

Thr Tyr Asp Ser Asn Cys Ala Ala Cys His Gln Pro Asp Gly Lys Gly
                405                 410                 415

Val Pro Asn Ala Phe Pro Pro Leu Ala Asn Ser Asp Tyr Leu Asn Ala
            420                 425                 430

Asp His Ala Arg Ala Ala Ser Ile Val Ala Asn Gly Leu Ser Gly Lys
        435                 440                 445

Ile Thr Val Asn Gly Asn Gln Tyr Glu Ser Val Met Pro Ala Ile Ala
    450                 455                 460

Leu Ser Asp Gln Gln Ile Ala Asn Val Ile Thr Tyr Thr Leu Asn Ser
465                 470                 475                 480

Phe Gly Asn Lys Gly Gly Gln Leu Ser Ala Asp Asp Val Ala Lys Ala
                485                 490                 495

Lys Lys Thr Lys Pro Asn
            500
```

<210> SEQ ID NO 3

-continued

<211> LENGTH: 1506
<212> TYPE: DNA
<213> ORGANISM: Moraxella catarrhalis

<400> SEQUENCE: 3

```
atgtctaagc ctactttgat aaaaacaacc ttaatttgtg ccttaagtgc attgatgctc     60

agtggttgta gcaatcaagc ggacaaagcc gcccagccaa aaagcagcac ggtagacgct    120

gccgccaaga cagcaaatgc agataatgct gcctcacaag aacatcaagg cgagctgcct    180

gtcattgatg ccattgttac gcatgcacca gaagttccac cacctgttga ccgtgaccac    240

cccgccaaag tggtggtaaa aatggaaacc gttgaaaaag tcatgcgtct ggcagatggc    300

gtggaatatc agttttggac atttggcggt caagttccag ggcagatgat tcgtgtgcgt    360

gaaggcgaca ccatcgaagt gcagttctca aaccacccag attcaaaaat gccccataat    420

gttgactttc acgctgccac agggcctggc ggcggggcag aagcgtcatt taccgcaccg    480

ggtcatacat caacctttag ttttaaagcc ttacagcctg gtttgtatgt ctatcactgt    540

gcggttgccc ctgttggcat gcacattgct aatggcatgt atggtttgat tttggttgaa    600

ccaaaagagg gcttgccaaa agtagataaa gaatactatg tcatgcaagg cgacttttat    660

accaaaggca aatatggcga acaaggtcta cagccctttg atatggaaaa agccattcga    720

gaagatgctg aatatgttgt ctttaatggt tcggtggggg cgttgactgg tgaaaatgct    780

ctaaaagcca aggttggcga aactgttcgc ttatttgtgg gtaacggcgg cccgaatttg    840

acatcatcat tccatgtcat tggtgagatt tttgataagg ttcactttga gggtggtaag    900

ggtgaaaacc acaatatcca aaccacgcta atcccagcag gtggcgctgc catcactgaa    960

tttaaggtgg atgtgccggg tgattatgtc ttggttgacc atgccatctt ccgtgccttt   1020

aacaaagggg cattgggcat acttaaggtg gaaggtgaag aaaatcatga gatttattca   1080

cacaaacaaa cagacgctgt ctatctgcca gagggtgccc cacaagcaat tgatacccaa   1140

gaagcaccca aaacacctgc acctgccaac ttacaagagc agattaaagc aggtaaggca   1200

acctatgact ctaactgtgc tgcttgtcac caacctgatg gtaaaggcgt gccaaacgct   1260

ttcccaccgc ttgccaactc tgactatctg aacgccgacc acgctcgtgc cgccagcatc   1320

gtggcaaatg gattgtctgg taagattacc gtcaatggca accaatatga aagcgtcatg   1380

cctgcgattg ctctgagcga ccaacagatt gccaatgtca tcacctacac gcttaacagc   1440

tttggtaaca aaggcggtca actcagtgca gacgatgtgg caaaagccaa aaaaaccaag   1500

ccaaac                                                               1506
```

<210> SEQ ID NO 4
<211> LENGTH: 502
<212> TYPE: PRT
<213> ORGANISM: Moraxella catarrhalis

<400> SEQUENCE: 4

```
Met Ser Lys Pro Thr Leu Ile Lys Thr Thr Leu Ile Cys Ala Leu Ser
 1               5                  10                  15

Ala Leu Met Leu Ser Gly Cys Ser Asn Gln Ala Asp Lys Ala Ala Gln
            20                  25                  30

Pro Lys Ser Ser Thr Val Asp Ala Ala Ala Lys Thr Ala Asn Ala Asp
        35                  40                  45

Asn Ala Ala Ser Gln Glu His Gln Gly Glu Leu Pro Val Ile Asp Ala
    50                  55                  60

Ile Val Thr His Ala Pro Glu Val Pro Pro Pro Val Asp Arg Asp His
```

-continued

```
65                  70                  75                  80

Pro Ala Lys Val Val Val Lys Met Glu Thr Val Glu Lys Val Met Arg
                85                  90                  95

Leu Ala Asp Gly Val Glu Tyr Gln Phe Trp Thr Phe Gly Gly Gln Val
            100                 105                 110

Pro Gly Gln Met Ile Arg Val Arg Glu Gly Asp Thr Ile Glu Val Gln
        115                 120                 125

Phe Ser Asn His Pro Asp Ser Lys Met Pro His Asn Val Asp Phe His
    130                 135                 140

Ala Ala Thr Gly Pro Gly Gly Gly Ala Glu Ala Ser Phe Thr Ala Pro
145                 150                 155                 160

Gly His Thr Ser Thr Phe Ser Phe Lys Ala Leu Gln Pro Gly Leu Tyr
                165                 170                 175

Val Tyr His Cys Ala Val Ala Pro Val Gly Met His Ile Ala Asn Gly
            180                 185                 190

Met Tyr Gly Leu Ile Leu Val Glu Pro Lys Glu Gly Leu Pro Lys Val
        195                 200                 205

Asp Lys Glu Tyr Tyr Val Met Gln Gly Asp Phe Tyr Thr Lys Gly Lys
    210                 215                 220

Tyr Gly Glu Gln Gly Leu Gln Pro Phe Asp Met Glu Lys Ala Ile Arg
225                 230                 235                 240

Glu Asp Ala Glu Tyr Val Val Phe Asn Gly Ser Val Gly Ala Leu Thr
                245                 250                 255

Gly Glu Asn Ala Leu Lys Ala Lys Val Gly Glu Thr Val Arg Leu Phe
            260                 265                 270

Val Gly Asn Gly Gly Pro Asn Leu Thr Ser Ser Phe His Val Ile Gly
        275                 280                 285

Glu Ile Phe Asp Lys Val His Phe Glu Gly Gly Lys Gly Glu Asn His
    290                 295                 300

Asn Ile Gln Thr Thr Leu Ile Pro Ala Gly Gly Ala Ala Ile Thr Glu
305                 310                 315                 320

Phe Lys Val Asp Val Pro Gly Asp Tyr Val Leu Val Asp His Ala Ile
                325                 330                 335

Phe Arg Ala Phe Asn Lys Gly Ala Leu Gly Ile Leu Lys Val Glu Gly
            340                 345                 350

Glu Glu Asn His Glu Ile Tyr Ser His Lys Gln Thr Asp Ala Val Tyr
        355                 360                 365

Leu Pro Glu Gly Ala Pro Gln Ala Ile Asp Thr Gln Glu Ala Pro Lys
    370                 375                 380

Thr Pro Ala Pro Ala Asn Leu Gln Glu Gln Ile Lys Ala Gly Lys Ala
385                 390                 395                 400

Thr Tyr Asp Ser Asn Cys Ala Ala Cys His Gln Pro Asp Gly Lys Gly
                405                 410                 415

Val Pro Asn Ala Phe Pro Pro Leu Ala Asn Ser Asp Tyr Leu Asn Ala
            420                 425                 430

Asp His Ala Arg Ala Ala Ser Ile Val Ala Asn Gly Leu Ser Gly Lys
        435                 440                 445

Ile Thr Val Asn Gly Asn Gln Tyr Glu Ser Val Met Pro Ala Ile Ala
    450                 455                 460

Leu Ser Asp Gln Gln Ile Ala Asn Val Ile Thr Tyr Thr Leu Asn Ser
465                 470                 475                 480

Phe Gly Asn Lys Gly Gly Gln Leu Ser Ala Asp Asp Val Ala Lys Ala
                485                 490                 495
```

-continued

```
Lys Lys Thr Lys Pro Asn
            500


<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5

aagcgaacag tttcgccaac c                                               21


<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6

gggggcgttg actggtgaaa atg                                             23


<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7

gtaaaacgac ggccagt                                                    17


<210> SEQ ID NO 8
<211> LENGTH: 17
<212> TYPE: DNA
<213> ORGANISM: Artificial Sequence
<220> FEATURE:
<223> OTHER INFORMATION: primer

<400> SEQUENCE: 8

caggaaacag ctatgac                                                    17


<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9

acatgtctaa gcctactttg at                                              22


<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10

agatctgttt ggcttggttt ttttggc                                         27
```

MORAXELLA CATARRHALIS ANTIGEN, CORRESPONDING GENE AND USES THEREOF

This application is a National Phase Application of WO 01/19996, and claims priority of GB 9921691.3; filed 14 Sep. 1999.

FIELD OF THE INVENTION

This invention relates to polynucleotides, (herein referred to as "BASB109 polynucleotide(s)"), polypeptides encoded by them (referred to herein as "BASB109" or "BASB109 polypeptide(s)"), recombinant materials and methods for their production. In another aspect, the invention relates to methods for using such polypeptides and polynucleotides, including vaccines against bacterial infections. In a further aspect, the invention relates to diagnostic assays for detecting infection of certain pathogens.

BACKGROUND OF THE INVENTION

*Moraxella catarrhalis* (also named *Branhamella catarrhalis*) is a Gram negative bacteria frequently isolated from the human upper respiratory tract. It is responsible for several pathologies the main ones being otitis media in infants and children, and pneumonia in elderlies. It is also responsible of sinusitis, nosocomial infections and less frequently of invasive diseases.

Otitis media is an important childhood disease both by the number of cases and its potential sequelae. More than 3.5 millions cases are recorded every year in the United States, and it is estimated that 80% of the children have experienced at least one episode of otitis before reaching the age of 3 (Klein, J O (1994) Clin. Inf. Dis 19:823). Left untreated, or becoming chronic, this disease may lead to hearing losses that could be temporary (in the case of fluid accumulation in the middle ear) or permanent (if the auditive nerve is damaged). In infants, such hearing losses may be responsible for a delayed speech learning.

Three bacterial species are primarily isolated from the middle ear of children with otitis media: *Streptococcus pneumoniae*, non typeable *Haemophilus influenza* (NTHi) and *M. catarrhalis*. They are present in 60 to 90% of the cases. A review of recent studies shows that *S. pneumoniae* and NTHi represent both about 30%, and *M. catarrhalis* about 15% of the otitis media cases (Murphy, T F (1996) Microbiol. Rev. 60:267). Other bacteria could be isolated from the middle ear (*H. influenza* type B, *S. pyogenes* etc) but at a much lower frequency (2% of the cases or less).

Epidemiological data indicate that, for the pathogens found in the middle ear, the colonization of the upper respiratory tract is an absolute prerequisite for the development of an otitis; other are however also required to lead to the disease (Dickinson, D P et al. (1988) J. Infect. Dis. 158:205, Faden, H L et al. (1991) Ann. Otorhinol. Laryngol. 100:612). These are important to trigger the migration of the bacteria into the middle ear via the Eustachian tubes, followed by the initiation of an inflammatory process. These factors are unknown todate. It has been postulated that a transient anomaly of the immune system following a viral infection, for example, could cause an inability to control the colonization of the respiratory tract (Faden, H L et al (1994) J. Infect. Dis. 169:1312). An alternative explanation is that the exposure to environmental factors allow a more important colonization of some children, who subsequently become susceptible to the development of otitis media because of the sustained presence of middle ear pathogens (Murphy, T F (1996) Microbiol. Rev. 60:267).

The immune response to *M. catarrhalis* is poorly characterized. The analysis of strains isolated sequentially from the nasopharynx of babies followed from 0 to 2 years of age, indicates that they get and eliminate frequently new strains. This indicates that an efficacious immune response against this bacteria is mounted by the colonized children (Faden, H L et al (1994) J. Infect. Dis. 169:1312).

In most adults tested, bactericidal antibodies have been identified (Chapman, A J et al. (1985) J. Infect. Dis. 151:878). Strains of *M. catarrhalis* present variations in their capacity to resist serum bactericidal activity: in general, isolates from diseased individuals are more resistant than those who are simply colonized (Hol, C et al. (1993) Lancet 341:1281, Jordan, K L et al. (1990) Am. J. Med. 88 (suppl. 5A):28S). Serum resistance could therefore be considered as a virulence factor of the bacteria. An opsonizing activity has been observed in the sera of children recovering from otitis media.

The antigens targeted by these different immune responses in humans have not been identified, with the exception of OMP B1, a 84 kDa protein which expression is regulated by iron, and that is recognized by the sera of patients with pneumonia (Sethi, S, et al. (1995) Infect. Immun. 63:1516), and of UspA1 and UspA2 (Chen D. et al.(1999), Infect. Immun. 67:1310).

A few other membrane proteins present on the surface of *M. catarrhalis* have been characterized using biochemical method, or for their potential implication in the induction of a protective immunity (for review, see Murphy, T F (1996) Microbiol. Rev. 60:267). In a mouse pneumonia model, the presence of antibodies raised against some of them (UspA, CopB) favors a faster clearance of the pulmonary infection. Another polypeptide (OMP CD) is highly conserved among *M. catarrhalis* strains, and presents homologies with a porin of *Pseudomonas aeruginosa*, which has been demonstrated efficacious against this bacterium in animal models.

The frequency of *Moraxella catarrhalis* infections has risen dramatically in the past few decades. This has been attributed to the emergence of multiply antibiotic resistant strains and an increasing population of people with weakened immune systems. It is no longer uncommon to isolate *Moraxella catarrhalis* strains that are resistant to some or all of the standard antibiotics. This phenomenon has created an unmet medical need and demand for new anti-microbial agents, vaccines, drug screening methods, and diagnostic tests for this organism.

SUMMARY OF THE INVENTION

The present invention relates to BASB109, in particular BASB109 polypeptides and BASB109 polynucleotides, recombinant materials and methods for their production. In another aspect, the invention relates to methods for using such polypeptides and polynucleotides, including prevention and treatment of microbial diseases, amongst others. In a further aspect, the invention relates to diagnostic assays for detecting diseases associated with microbial infections and conditions associated with such infections, such as assays for detecting expression or activity of BASB109 polynucleotides or polypeptides.

Various changes and modifications within the spirit and scope of the disclosed invention will become readily apparent to those skilled in the art from reading the following descriptions and from reading the other parts of the present disclosure.

BRIEF DESCRIPTION OF THE DRAWINGS

FIGS. 1A–1H show consecutive, aligned segments for two BASB109 polynucleotides, SEQ ID NO:1 and SEQ ID NO:3.

FIG. 2A–2D show consecutive, aligned segments for two BASB109 polpeptides, SEQ ID NO:2 and SEQ ID NO:4.

FIG. 3A shows a Coomassie stained SDS-polyacrylamide gel of purified BASB109 polypeptide. FIG. 3B shows a Western blot of purified BASB109 polypeptide stained with anti-His antibody.

DESCRIPTION OF THE INVENTION

The invention relates to BASB109 polypeptides and polynucleotides as described in greater detail below. In particular, the invention relates to polypeptides and polynucleotides of BASB109 of *Moraxella catarrhalis*, which is related by amino acid sequence homology to *Neisseria gonorrheae* major anaerobically induced outer membrane protein. The invention relates especially to BASB109 having the nucleotide and amino acid sequences set out in SEQ ID NO:1 or 3 and SEQ ID NO:2 or 4 respectively. It is understood that sequences recited in the Sequence Listing below as "DNA" represent an exemplification of one embodiment of the invention, since those of ordinary skill will recognize that such sequences can be usefully employed in polynucleotides in general, including ribopolynucleotides.

Polypeptides

In one aspect of the invention there are provided polypeptides of *Moraxella catarrhalis* referred to herein as "BASB109" and "BASB109 polypeptides" as well as biologically, diagnostically, prophylactically, clinically or therapeutically useful variants thereof, and compositions comprising the same.

The present invention further provides for:

(a) an isolated polypeptide which comprises an amino acid sequence which has at least 85% identity, preferably at least 90% identity, more preferably at least 95% identity, most preferably at least 97–99% or exact identity, to that of SEQ ID NO:2 or 4;

(b) a polypeptide encoded by an isolated polynucleotide comprising a polynucleotide sequence which has at least 85% identity, preferably at least 90% identity, more preferably at least 95% identity, even more preferably at least 97–99% or exact identity to SEQ ID NO:1 or 3 over the entire length of SEQ ID NO:1 or 3 respectively; or (c) a polypeptide encoded by an isolated polynucleotide comprising a polynucleotide sequence encoding a polypeptide which has at least 85% identity, preferably at least 90% identity, more preferably at least 95% identity, even more preferably at least 97–99% or exact identity, to the amino acid sequence of SEQ ID NO:2 or 4.

The BASB109 polypeptides provided in SEQ ID NO:2 or 4 are the BASB109 polypeptides from *Moraxella catarrhalis* strain Mc2931 (ATCC 43617).

The invention also provides an immunogenic fragment of a BASB109 polypeptide, that is, a contiguous portion of the BASB109 polypeptide which has the same or substantially the same immunogenic activity as the polypeptide comprising the amino acid sequence of SEQ ID NO:2 or 4; That is to say, the fragment (if necessary when coupled to a carrier) is capable of raising an immune response which recognises the BASB109 polypeptide. Such an immunogenic fragment may include, for example, the BASB109 polypeptide lacking an N-terminal leader sequence, and/or a transmembrane domain and/or a C-terminal anchor domain. In a preferred aspect the immunogenic fragment of BASB109 according to the invention comprises substantially all of the extracellular domain of a polypeptide which has at least 85% identity, preferably at least 90% identity, more preferably at least 95% identity, most preferably at least 97–99% identity, to that of SEQ ID NO:2 or 4 over the entire length of SEQ ID NO:2

A fragment is a polypeptide having an amino acid sequence that is entirely the same as part but not all of any amino acid sequence of any polypeptide of the invention. As with BASB109 polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of SEQ ID NO:2 or 4 or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2 or 4, or an isolated polypeptide comprising an amino acid sequence having at least 15, 20, 30, 40, 50 or 100 contiguous amino acids truncated or deleted from the amino acid sequence of SEQ ID NO:2 or 4.

Fragments of the polypeptides of the invention may be employed for producing the corresponding full-length polypeptide by peptide synthesis; therefore, these fragments may be employed as intermediates for producing the full-length polypeptides of the invention.

Particularly preferred are variants in which several, 5–10, 1–5, 1–3, 1–2 or 1 amino acids are substituted, deleted, or added in any combination.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* and the non-structural protein from influenzae virus, NS1 (hemagglutinin). Another fusion partner is the protein known as LytA. Preferably the C terminal portion of the molecule is used. Lyta is derived from *Streptococcus pneumoniae* which synthesize an N-acetyl-L-alanine amidase, amidase LytA, (coded by the lytA gene {Gene, 43 (1986) page 265–272}) an autolysin that specifically degrades certain bonds in the peptidoglycan backbone. The C-terminal domain of the LytA protein is responsible for the affinity to the choline or to some choline analogues such as DEAE. This property has been exploited for the development of *E. coli* C-LytA expressing plasmids useful for expression of fusion proteins. Purification of hybrid proteins containing the C-LytA fragment at its amino terminus has been described {Biotechnology: 10, (1992) page 795–798}. It is possible to use the repeat portion of the LytA molecule found in the C terminal end starting at residue 178, for example residues 188–305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

It is most preferred that a polypeptide of the invention is derived from *Moraxella catarrhalis*, however, it may preferably be obtained from other organisms of the same taxonomic genus. A polypeptide of the invention may also be obtained, for example, from organisms of the same taxonomic family or order.

Polynucleotides

It is an object of the invention to provide polynucleotides that encode BASB109 polypeptides, particularly polynucleotides that encode the polypeptide herein designated BASB109.

In a particularly preferred embodiment of the invention the polynucleotide comprises a region encoding BASB109 polypeptides comprising a sequence set out in SEQ ID NO:1 or 3 which includes a full length gene, or a variant thereof.

The BASB109 polynucleotides provided in SEQ ID NO:1 or 3 are the BASB109 polynucleotides from *Moraxella catarrhalis* strain Mc2931 (ATCC 43617).

As a further aspect of the invention there are provided isolated nucleic acid molecules encoding and/or expressing BASB109 polypeptides and polynucleotides, particularly *Moraxella catarrhalis* BASB109 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB109 polypeptide having a deduced amino acid sequence of SEQ ID NO:2 or 4 and polynucleotides closely related thereto and variants thereof.

In another particularly preferred embodiment of the invention there is a BASB109 polypeptide from *Moraxella catarrhalis* comprising or consisting of an amino acid sequence of SEQ ID NO:2 or 4 or a variant thereof.

Using the information provided herein, such as a polynucleotide sequence set out in SEQ ID NO:1 or 3, a polynucleotide of the invention encoding BASB109 polypeptide may be obtained using standard cloning and screening methods, such as those for cloning and sequencing chromosomal DNA fragments from bacteria using *Moraxella catarrhalis* Catlin cells as starting material, followed by obtaining a full length clone. For example, to obtain a polynucleotide sequence of the invention, such as a polynucleotide sequence given in SEQ ID NO:1 or 3, typically a library of clones of chromosomal DNA of *Moraxella catarrhalis* Catlin in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:1 or 3 was discovered in a DNA library derived from *Moraxella catarrhalis.*

Moreover, each DNA sequence set out in SEQ ID NO:1 or 3 contains an open reading frame encoding a protein having about the number of amino acid residues set forth in SEQ ID NO:2 or 4 with a deduced molecular weight that can be calculated using amino acid residue molecular weight values well known to those skilled in the art.

The polynucleotide of SEQ ID NO:1, between the start codon at nucleotide number 1 and the stop codon which begins at nucleotide number 1507 of SEQ ID NO:1, encodes the polypeptide of SEQ ID NO:2.

The polynucleotide of SEQ ID NO:3, between the start codon at nucleotide number 1 and the stop codon which begins at nucleotide number 1504 of SEQ ID NO:3, encodes the polypeptide of SEQ ID NO:4.

In a further aspect, the present invention provides for an isolated polynucleotide comprising or consisting of:

(a) a polynucleotide sequence which has at least 85% identity, preferably at least 90% identity, more preferably at least 95% identity, even more preferably at least 97–99% or exact identity to SEQ ID NO:1 or 3 over the entire length of SEQ ID NO:1 or 3 respectively; or (b) a polynucleotide sequence encoding a polypeptide which has at least 85% identity, preferably at least 90% identity, more preferably at least 95% identity, even more preferably at least 97–99% or 100% exact, to the amino acid sequence of SEQ ID NO:2 or 4, over the entire length of SEQ ID NO:2 or 4 respectively.

A polynucleotide encoding a polypeptide of the present invention, including homologs and orthologs from species other than *Moraxella catarrhalis*, may be obtained by a process which comprises the steps of screening an appropriate library under stringent hybridization conditions (for example, using a temperature in the range of 45–65° C. and an SDS concentration from 0.1–1%) with a labeled or detectable probe consisting of or comprising the sequence of SEQ ID NO:1 or 3 or a fragment thereof; and isolating a full-length gene and/or genomic clones containing said polynucleotide sequence.

The invention provides a polynucleotide sequence identical over its entire length to a coding sequence (open reading frame) in SEQ ID NO:1 or 3. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB109 polypeptide of SEQ ID NO:2 or 4 may be identical to the polypeptide encoding sequence contained in nucleotides 1 to 1506 of SEQ ID NO:1 or the polypeptide encoding sequence contained in nucleotides 1 to 1506 of SEQ ID NO:3 respectively. Alternatively it may be a sequence, which as a result of the redundancy (degeneracy) of the genetic code, also encodes the polypeptide of SEQ ID NO:2 or 4.

The term "polynucleotide encoding a polypeptide" as used herein encompasses polynucleotides that include a sequence encoding a polypeptide of the invention, particularly a bacterial polypeptide and more particularly a polypeptide of the *Moraxella catarrhalis* BASB109 having an amino acid sequence set out in SEQ ID NO:2 or 4. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:2 or 4. Fragments of polynucleotides of the invention may be used, for example, to synthesize full-length polynucleotides of the invention.

Further particularly preferred embodiments are polynucleotides encoding BASB109 variants, that have the amino acid sequence of BASB109 polypeptide of SEQ ID NO:2 or 4 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB109 polypeptide.

Further preferred embodiments of the invention are polynucleotides that are at least 85% identical over their entire length to a polynucleotide encoding BASB109 polypeptide having an amino acid sequence set out in SEQ ID NO:2 or 4, and polynucleotides that are complementary to such polynucleotides. Alternatively, most highly preferred are polynucleotides that comprise a region that is at least 90% identical over its entire length to a polynucleotide encoding BASB109 polypeptide and polynucleotides complementary thereto. In this regard, polynucleotides at least 95% identical over their entire length to the same are particularly preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:1 or 3.

In accordance with certain preferred embodiments of this invention there are provided polynucleotides that hybridize, particularly under stringent conditions, to BASB109 polynucleotide sequences, such as those polynucleotides in SEQ ID NO:1 or 3.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1 or 3 under stringent hybridization conditions with a probe having the sequence of said polynucleotide sequence set forth in SEQ ID NO:1 or 3 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB109 and to isolate cDNA and genomic clones of other genes that have a high identity, particularly high sequence identity, to the BASB109 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB109 gene may be isolated by screening using a DNA sequence provided in SEQ ID NO:1 or 3 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NOS:1 or 3 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., *Hum Mol Genet* (1992) 1: 363, Manthorpe et al., *Hum. Gene Ther*. (1983) 4: 419), delivery of DNA complexed with specific protein carriers (Wu et al., *J Biol Chem*. (1989) 264: 16985), coprecipitation of DNA with calcium phosphate (Benvenisty & Reshef, *PNAS USA*, (1986) 83: 9551), encapsulation of DNA in various forms of liposomes (Kaneda et al., *Science* (1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci, *E. coli*, streptomyces, cyanobacteria, *Bacillus subtilis, Neisseria meningitidis* and *Moraxella catarrhalis*; fungal cells, such as cells of a yeast, Kluveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox), alphaviruses (Sindbis virus, Semliki Forest Virus, Venezuelian Equine Encephalitis Virus), adenoviruses, adeno-associated virus, picornaviruses (poliovirus, rhinovirus), herpesviruses (varicella zoster virus, etc), Listeria, Salmonella, Shigella, BCG. These viruses and bacteria can be virulent, or attenuated in various ways in order to obtain live vaccines. Such live vaccines also form part of the invention.

Diagnostic, Prognostic, Serotyping and Mutation Assays

This invention is also related to the use of BASB109 polynucleotides and polypeptides of the invention for use as diagnostic reagents. Detection of BASB109 polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the BASB109 gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled BASB109 polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA*, 85: 4397–4401 (1985).

In another embodiment, an array of oligonucleotides probes comprising BASB109 nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science*, 274: 610 (1996)).

Thus in another aspect, the present invention relates to a diagnostic kit which comprises:

(a) a polynucleotide of the present invention, preferably the nucleotide sequence of SEQ ID NO:1 or 3, or a fragment thereof;

(b) a nucleotide sequence complementary to that of (a);

(c) a polypeptide of the present invention, preferably the polypeptide of SEQ ID NO:2 or 4 or a fragment thereof; or (d) an antibody to a polypeptide of the present invention, preferably to the polypeptide of SEQ ID NO:2 or 4.

It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferably SEQ ID NO:1 or 3, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (alletic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding BASB109 polypeptide can be used to identify and analyze mutations.

The invention further provides primers with 1, 2, 3 or 4 nucleotides removed from the 5' and/or the 3' end. These primers may be used for, among other things, amplifying BASB109 DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by *Moraxella catarrhalis*, comprising determining from a sample derived from an individual, such as a bodily material, an increased level of expression of polynucleotide having a sequence of SEQ ID NO:1 or 3. Increased or decreased expression of a BASB109 polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of BASB109 polypeptide compared to normal control tissue samples may be used to detect the presence of an infection, for example. Assay techniques that can be used to determine levels of a BASB109 polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probes obtained or derived from a bodily sample, to determine the presence of a particular polynucleotide sequence or related sequence in an individual. Such a presence may indicate the presence of a pathogen, particularly *Moraxella catarrhalis*, and may be useful in diagnosing and/or prognosing disease or a course of disease. A grid comprising a number of variants of the polynucleotide sequence of SEQ ID NO:1 or 3 are preferred. Also preferred is a comprising a number of variants of a polynucleotide sequence encoding the polypeptide sequence of SEQ ID NO:2 or 4.

Antibodies

The polypeptides and polynucleotides of the invention or variants thereof, or cells expressing the same can be used as immunogens to produce antibodies immunospecific for such polypeptides or polynucleotides respectively. The term "immunospecific" means that the antibodies have substantially greater affinity for the polypeptides of the invention than their affinity for other related polypeptides in the prior art.

In certain preferred embodiments of the invention there are provided antibodies against BASB109 polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used Examples include various techniques, such as those in Kohler, G. and Milstein, C., *Nature* 256: 495497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-BASB109 or from naive libraries (McCafferty, et al., (1990), *Nature* 348, 552–554; Marks, et al., (1992) *Biotechnology* 10, 779–783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against BASB109-polypeptide or BASB109-polynucleotide may be employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be "humanized," where the complimentarily determining region or regions of the hybridoma-derived antibody has been transplanted into a human monoclonal antibody, for example as described in Jones et al. (1986), *Nature* 321, 522–525 or Tempest et al., (1991) *Biotechnology* 9, 266–273.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring BASB109 polypeptide and/or polynucleotide activity in the mixture, and comparing the BASB109 polypeptide and/or polynucleotide activity of the mixture to a standard. Fusion proteins, such as those made from Fc portion and BASB109 polypeptide, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., J Biol Chem, 270(16) :9459–9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of BASB109 polypeptides or polynucleotides, particularly those compounds that are bacteriostatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising BASB109 polypeptide and a labeled substrate or ligand of such polypeptide is incubated in the absence or the presence of a candidate molecule that may be a BASB109 agonist or antagonist. The ability of the candidate molecule to agonize or antagonize the BASB109 polypeptide is reflected in decreased binding of the labeled ligand or decreased production of product from such substrate. Molecules that bind gratuitously, i.e., without inducing the effects of BASB109 polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in BASB109 polynucleotide or polypeptide activity, and binding assays known in the art.

Another example of an assay for BASB109 agonists is a competitive assay that combines BASB109 and a potential agonist with BASB109-binding molecules, recombinant BASB109 binding molecules, natural substrates or ligands, or substrate or ligand mimetics, under appropriate conditions for a competitive inhibition assay. BASB109 can be labeled, such as by radioactivity or a calorimetric compound, such that the number of BASB109 molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing BASB109-induced activities, thereby preventing the action or expression of BASB109 polypeptides and/or polynucleotides by excluding BASB109 polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of BASB109.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial BASB109 proteins that mediate tissue damage and/or, to block the normal progression of pathogenesis in infections initiated other than by the implantation of in-dwelling devices or by other surgical techniques.

In accordance with yet another aspect of the invention, there are provided BASB109 agonists and antagonists, preferably bacteristatic or bactericidal agonists and antagonists.

The antagonists and agonists of the invention may be employed, for instance, to prevent, inhibit and/or treat diseases.

In a further aspect, the present invention relates to mimotopes of the polypeptide of the invention. A mimotope is a peptide sequence, sufficiently similar to the native peptide (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with BASB109 polynucleotide and/or polypeptide, or a fragment or variant thereof, adequate to produce antibody and/ or T cell immune response to protect said individual from infection, particularly bacterial infection and most particularly *Moraxella catarrhalis* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of BASB109 polynucleotide and/or polypeptide, or a fragment or a variant thereof, for expressing BASB109 polynucleotide and/or polypeptide, or a fragment or a variant thereof in vivo in order to induce an immunological response, such as, to produce antibody and/ or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a BASB109 polynucleotide and/or polypeptide encoded therefrom, wherein the composition comprises a recombinant BASB109 polynucleotide and/or polypeptide encoded therefrom and/or comprises DNA and/or RNA which encodes and expresses an antigen of said BASB109 polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+ T cells.

A BASB109 polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Haemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein In a vaccine composition according to the invention, a BASB109 polypeptide and/or polynucleotide, or a fragment, or a mimotope, or a variant thereof may be present in a vector, such as the live recombinant vectors described above for example live bacterial vectors.

Also suitable are non-live vectors for the BASB109 polypeptide, for example bacterial outer-membrane vesicles or "blebs". OM blebs are derived from the outer membrane of the two-layer membrane of Gram-negative bacteria and have been documented in many Gram-negative bacteria (Zhou, L et al. 1998. *FEMS Microbiol. Lett.* 163:223–228) including *C. trachomatis* and *C. psittaci.* A non-exhaustive list of bacterial pathogens reported to produce blebs also includes: *Bordetella pertussis, Borrelia burgdorferi, Brucella melitensis, Brucella ovis, Esherichia coli, Haemophilus influenza, Legionella pneumophila, Moraxella catarrhalis, Neisseria gonorrhoeae, Neisseria meningitidis, Pseudomonas aeruginosa* and *Yersinia enterocolitica.*

Blebs have the advantage of providing outer-membrane proteins in their native conformation and are thus particularly useful for vaccines. Blebs can also be improved for vaccine use by engineering the bacterium so as to modify the expression of one or more molecules at the outer membrane. Thus for example the expression of a desired immunogenic protein at the outer membrane, such as the BASB109 polypeptide, can be introduced or upregulated (e.g. by altering the promoter). Instead or in addition, the expression of outer-membrane molecules which are either not relevant (e.g. unprotective antigens or immunodominant but variable proteins) or detrimental (e.g. toxic molecules such as LPS, or potential inducers of an autoimmune response) can be downregulated. These approaches are discussed in more detail below.

The non-coding flanking regions of the BASB109 gene contain regulatory elements important in the expression of the gene. This regulation takes place both at the transcriptional and translational level. The sequence of these regions, either upstream or downstream of the open reading frame of the gene, can be obtained by DNA sequencing. This sequence information allows the determination of potential regulatory motifs such as the different promoter elements, terminator sequences, inducible sequence elements, repressors, elements responsible for phase variation, the shine-dalgarno sequence, regions with potential secondary structure involved in regulation, as well as other types of regulatory motifs or sequences. This sequence is a further aspect of the invention.

This sequence information allows the modulation of the natural expression of the BASB109 gene. The upregulation of the gene expression may be accomplished by altering the promoter, the shine-dalgarno sequence, potential repressor or operator elements, or any other elements involved. Likewise, downregulation of expression can be achieved by similar types of modification. Alternatively, by changing phase variation sequences, the expression of the gene can be put under phase variation control, or it may be uncoupled from this regulation. In another approach, the expression of the gene can be put under the control of one or more inducible elements allowing regulated expression. Examples of such regulation include, but are not limited to, induction by temperature shift, addition of inductor substrates like selected carbohydrates or their derivatives, trace elements, vitamins, co-factors, metal ions, etc.

Such modifications as described above can be introduced by several different means. The modification of sequences involved in gene expression can be carried out in vivo by random mutagenesis followed by selection for the desired phenotype. Another approach consists in isolating the region of interest and modifying it by random mutagenesis, or site-directed replacement, insertion or deletion mutagenesis. The modified region can then be reintroduced into the bacterial genome by homologous recombination, and the effect on gene expression can be assessed. In another approach, the sequence knowledge of the region of interest can be used to replace or delete all or part of the natural regulatory sequences. In this case, the regulatory region targeted is isolated and modified so as to contain the regulatory elements from another gene, a combination of regulatory elements from different genes, a synthetic regulatory region, or any other regulatory region, or to delete selected parts of the wild-type regulatory sequences. These modified sequences can then be reintroduced into the bacterium via homologous recombination into the genome. A non-exhaustive list of preferred promoters that could be used for up-regulation of gene expression includes the promoters porA, porB, lbpB, tbpB, p110, lst, hpuAB from *N. meningitidis* or *N. gonorroheae*; ompCD, copB, lbpB, ompE, UspA1; UspA2; TbpB from *M. Catarrhalis*; p1, p2, p4, p5, p6, IpD, tbpB, D15, Hia, Hmw1, Hmw2 from *H. influenzae.*

In one example, the expression of the gene can be modulated by exchanging its promoter with a stronger promoter (through isolating the upstream sequence of the gene, in vitro modification of this sequence, and reintroduction into the genome by homologous recombination). Upregulated expression can be obtained in both the bacterium as well as in the outer membrane vesicles shed (or made) from the bacterium.

In other examples, the described approaches can be used to generate recombinant bacterial strains with improved characteristics for vaccine applications. These can be, but are not limited to, attenuated strains, strains with increased expression of selected antigens, strains with knock-outs (or decreased expression) of genes interfering with the immune response, strains with modulated expression of immunodominant proteins, strains with modulated shedding of outer-membrane vesicles.

Thus, also provided by the invention is a modified upstream region of the BASB109 gene, which modified upstream region contains a heterologous regulatory element which alters the expression level of the BASB109 protein located at the outer membrane. The upstream region according to this aspect of the invention includes the sequence upstream of the BASB109 gene. The upstream region starts immediately upstream of the BASB109 gene and continues usually to a position no more than about 1000 bp upstream of the gene from the ATG start codon. In the case of a gene located in a polycistronic sequence (operon) the upstream region can start immediately preceding the gene of interest, or preceding the first gene in the operon. Preferably, a modified upstream region according to this aspect of the invention contains a heterologous promotor at a position between 500 and 700 bp upstream of the ATG.

Thus, the invention provides a BASB109 polypeptide, in a modified bacterial bleb. The invention further provides modified host cells capable of producing the non-live membrane-based bleb vectors. The invention further provides nucleic acid vectors comprising the BASB109 gene having a modified upstream region containing a heterologous regulatory element.

Further provided by the invention are processes to prepare the host cells and bacterial blebs according to the invention.

Also provided by this invention are compositions, particularly vaccine compositions, and methods comprising the polypeptides and/or polynucleotides of the invention and immunostimulatory DNA sequences, such as those described in Sato, Y. et al. Science 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with *Moraxella catarrhalis*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Moraxella catarrhalis* infection, in mammals, particularly humans.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. *Annual Review of Immunology*, 7, p145–173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2-type responses are associated with the secretion of IL-4, IL-5, IL-6 and IL-13.

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454). 3D-MPL will be present in the range of 10 μg–100 μg preferably 25–50 μg per dose wherein the antigen will typically be present in a range 2–50 μg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with an carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:1 3D-MPL:QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 μg–200 μg, such as 10–100 μg, preferably 10 μg–50 μg per dose. Typically the oil in water will comprise from 2 to 10% squalene, from 2 to 10% alpha tocopherol and from 0.3 to 3% tween 80. Preferably the ratio of squalene:alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

While the invention has been described with reference to certain BASB109 polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

Compositions, Kits and Administration

In a further aspect of the invention there are provided compositions comprising a BASB109 polynucleotide and/or a BASB109 polypeptide for administration to a cell or to a multicellular organism.

The invention also relates to compositions comprising a polynucleotide and/or a polypeptides discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, codon usage analysis, nucleic acid base trimming, and sequencing chromatogram peak analysis.

A computer based method is provided for performing homology identification. This method comprises the steps of: providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Definitions

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math*., 48: 1073 (1988). Methods to determine identity are designed to give the largest match between the sequences tested. Moreover, methods to determine identity are codified in publicly available computer programs.

Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J. Molec. Biol.* 215: 403–410 (1990), and FASTA(Pearson and Lipman Proc. Natl. Acad. Sci. USA 85; 2444–2448 (1988). The BLAST family of programs is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following:

Algorithm: Needleman and Wunsch, J. Mol Biol. 48: 443–453 (1970)

Comparison matrix: BLOSSUM62 from Henikoff and Henikoff,

Proc. Natl. Acad. Sci. USA. 89:10915–10919 (1992)

Gap Penalty: 8

Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leqq x_n - (x_n \cdot y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leqq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leqq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leqq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which may be unmodified RNA or DNA or modified RNA or DNA including single and double-stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by a bacteria, including, for example, otitis media in infants and children, pneumonia in elderlies, sinusitis, nosocomial infections and invasive diseases, chronic otitis media with hearing loss, fluid accumulation in the middle ear, auditive nerve damage, delayed speech learning, infection of the upper respiratory tract and inflammation of the middle ear.

EXAMPLES

The examples below are carried out using standard techniques, which are well known and routine to those of skill in the art, except where otherwise described in detail. The examples are illustrative, but do not limit the invention.

Example 1

DNA Sequencing of the BASB109 Gene from *Moraxella catarrhalis* Strain ATCC 43617

A: BASB109 in *Moraxella catarrhalis* Strain.

The DNA sequence of the BASB109 gene from the *Moraxella catarrhalis* strain ATCC 43617 (also referred to as strain MC2931) is shown in SEQ ID NO:1. The translation of the BASB109 polynucleotide sequence showed in SEQ ID NO:2.

B: BASB109 in *Moraxella catarrhalis* Strain 43617.

The sequence of the BASB109 gene was confirmed in *Moraxella catarrhalis* strain ATCC 43617. For this purpose, plasmid DNA (see example 2A) containing the gene region encoding the mature BASB109 from *Moraxella catarrhalis* strain ATCC 43617 was submitted to DNA sequencing using the Big Dyes kit (Applied biosystems) and analyzed on a ABI 373/A DNA sequencer in the conditions described by the supplier using primers *Moraxella catarrhalis* oli 3 lipo5 (5'-AAG CGA ACA GTT TCG CCA ACC-3') [SEQ ID NO:5] and oli 4 lipo5 (5'-GGG GGC GTT GAC TGG TGA AAA TG-3') [SEQ ID NO:6] specific for the BASB109 gene and M13 Universal Sequence Primer (5'-GTA AAA CGA CGG CCA GT-3') [SEQ ID NO:7] and M13 Reverse Sequence Primer (5'-CAG GAA ACA GCT ATG AC-3') [SEQ ID NO:8] specific for the vector. As a result, the polynucleotide and deduced polypeptide sequences, referred to as SEQ ID NO:3 and SEQ ID NO:4 respectively, were obtained.

Using the MegAlign program from the DNASTAR software package, an alignment of the polynucleotide sequences of SEQ ID NO:1 and 3 was performed, and is displayed in FIG. 1; a pairwise comparison of identities shows that the two BASB109 polynucleotide gene sequences are 100% identical. Using the same MegAlign program, an alignment of the polypeptide sequences of SEQ ID NO:2 and 4 was performed, and is displayed in FIG. 2; a pairwise comparison of identities shows that the two BASB109 protein sequences are 100% identical.

Example 2

Construction of Plasmid to Express Recombinant BASB109

A: Cloning of BASB109.

The AflIII and BglII restriction sites engineered into the oli1 lipo 5 (5'-ACA TGT CTA AGC CTA CTT TGA T-3') [SEQ ID NO:9] forward and oli2 lipo 5 (5'-AGA TCT GTT TGG CTT GGT TTT TTT GGC-3') [SEQ ID NO:10] reverse amplification primers, respectively, permitted directional cloning of the PCR product into the *E. coli* expression plasmid pQE60 such that a mature BASB109 protein could be expressed as a fusion protein containing a (His)6 affinity chromatography tag at the C-terminus. The BASB109 PCR product was first introduced into the pCRIITOPO cloning vector (In vitrogen) using Top10 bacterial cells, according to the manufacturer's instructions. This intermediate construct was realized to facilitate further cloning into an expression vector. Transformants containing the BASB109 DNA insert were selected by restriction analysis. Following digestion, a ~20 $\mu$l aliquot of the reaction was analyzed by agarose gel electrophoresis (0.8% agarose in a Tris-acetate-EDTA (TAE) buffer). DNA fragments were visualized by UV illumination after gel electrophoresis and ethidium bromide staining. A DNA molecular size standard (1 Kb ladder, Life Technologies) was electrophoresed in parallel with the test samples and was used to estimate the size of the DNA fragments. Plasmid purified from selected transformants was then sequentially digested to completion with AflIII and BglII restriction enzymes as recommended by the manufacturer (Life Technologies). The digested DNA fragment was then purified using silica gel-based spin columns prior to ligation with the pQE60 plasmid.

B: Expression Analysis of PCR-Positive Transformants.

To prepare the expression plasmid pQE60 for ligation, it was similarly digested to completion with both NcoI and BglII and then treated with calf intestinal phosphatase (CIP, ~0.02 units/pmol of 5' end, Life Technologies) as directed by the manufacturer to prevent self ligation. An approximately 5-fold molar excess of the digested fragment to the prepared vector was used to program the ligation reaction. A standard ~20 μl ligation reaction (~16° C., ~16 hours), using methods well known in the art, was performed using T4 DNA ligase (~2.0 units/reaction, Life Technologies). An aliquot of the ligation (~5 μl) was used to transform electro-competent cells according to methods well known in the art. Following a ~2–3 hour outgrowth period at 37° C. in ~1.0 ml of LB broth, transformed cells were plated on LB agar plates containing ampicillin (100 μg/ml). Antibiotic was included in the selection. Plates were incubated overnight at 37° C. for ~16 hours. Individual ApR colonies were picked with sterile toothpicks and used to "patch" inoculate fresh LB ApR plates as well as a ~1.0 ml LB ApR broth culture. Both the patch plates and the broth culture were incubated overnight at 37° C. in either a standard incubator (plates) or a shaking water bath. Restriction analysis was then performed to verify that transformants contained the BASB109 DNA insert. Following digestion, a ~20 μl aliquot of the reaction was analyzed by agarose gel electrophoresis (0.8% agarose in a Tris-acetate-EDTA (TAE) buffer). DNA fragments were visualized by UV illumination after gel electrophoresis and ethidium bromide staining. A DNA molecular size standard (1 Kb ladder, Life Technologies) was electrophoresed in parallel with the test samples and was used to estimate the size of the DNA fragments. Transformants that produced the expected size DNA fragment were identified as strains containing a BASB109 expression construct. Expression plasmid containing strains were then analyzed for the inducible expression of recombinant BASB109.

C: Expression Analysis of PCR-Positive Transformants.

An aliquot (~1 μl) of the recombinant plasmid DNA preparations were then transformed into competent M15 (pREP4) bacterial cells according to methods well known in the art. Following a ~2–3 hour outgrowth period at 37° C. in ~1.0 ml of LB broth, transformed cells were plated on LB agar plates containing ampicillin (100 μg/ml) and kanamycin (30 μg/ml). Antibiotic was included in the selection. Plates were incubated overnight at 37° C. for ~16 hours. Individual ApR KmR colonies were picked with sterile toothpicks and used to inoculate ~5.0 ml LB ApR KmR broth culture. The broth cultures were incubated overnight at 37° C. with shaking (~250 rpm). An aliquot of the overnight seed culture (~1.0 ml) was inoculated into a 125 ml erlenmeyer flask containing ~25 ml of LB Ap broth and grown at 37° C. with shaking (~250 rpm) until the culture turbidity reached O.D.600 of ~0.5, i.e. mid-log phase (usually about 1.5–2.0 hours). At this time approximately half of the culture (~12.5 ml) was transferred to a second 125 ml flask and expression of recombinant BASB109 protein induced by the addition of IPTG (1.0 M stock prepared in sterile water, Sigma) to a final concentration of 1.0 mM. Incubation of both the IPTG-induced and non-induced cultures continued for an additional ~4 hours at 37° C. with shaking. Samples (~1.0 ml) of both induced and non-induced cultures were removed after the induction period and the cells collected by centrifugation in a microcentrifuge at room temperature for ~3 minutes. Individual cell pellets were suspended in ~50 μl of sterile water, then mixed with an equal volume of 2× Laemelli SDS-PAGE sample buffer containing 2-mercaptoethanol, and placed in boiling water bath for ~3 min to denature protein. Equal volumes (~15 μl) of both the crude IPTG-induced and the non-induced cell lysates were loaded onto duplicate 12% Tris/glycine polyacrylamide gel (1 mm thick Mini-gels, Novex). The induced and non-induced lysate samples were electrophoresed together with prestained molecular weight markers (SeeBlue, Novex) under conventional conditions using a standard SDS/Tris/glycine running buffer (BioRad). Following electrophoresis, one gel was stained with commassie brilliant blue R250 (BioRad) and then destained to visualize novel BASB109 IPTG-inducible protein(s). The second gel was electroblotted onto a PVDF membrane (0.45 micron pore size, Novex) for ~2 hrs at 4° C. using a BioRad Mini-Protean II blotting apparatus and Towbin's methanol (20%) transfer buffer. Blocking of the membrane and antibody incubations were performed according to methods well known in the art. A monoclonal anti-RGS (His)3 antibody, followed by a second rabbit anti-mouse antibody conjugated to HRP (QiaGen), was used to confirm the expression and identity of the BASB109 recombinant protein. Visualization of the anti-His antibody reactive pattern was achieved using either an ABT insoluble substrate or using Hyperfilm with the Amersham ECL chemiluminescence system.

Example 3

Production of Recombinant BASB109

Bacterial Strain

A recombinant expression strain of *E. coli* M15(pREP4) containing a plasmid (pQE60) encoding BASB109 from *M. catarrhalis* was used to produce cell mass for purification of recombinant protein. The expression strain was cultivated on LB agar plates containing 100 μg/ml ampicillin ("Ap") and 30 μg/ml kanamycin ("Km") to ensure that pQE60 and pREP4 were maintained. For cryopreservation at −80° C., the strain was propagated in LB broth containing the same concentration of antibiotics then mixed with an equal volume of LB broth containing 30% (w/v) glycerol.

Media

The fermentation medium used for the production of recombinant protein consisted of 2×YT broth (Difco) containing 100 μg/ml Ap and 30 μg/ml Km. Antifoam was added to medium for the fermentor at 0.25 ml/L (Antifoam 204, Sigma). To induce expression of the BASB109 recombinant protein, IPTG (Isopropyl β-D-Thiogalactopyranoside) was added to the fermentor (1 mM, final).

Fermentation

A 500-ml erlenmeyer seed flask, containing 50 ml working volume, was inoculated with 0.3 ml of rapidly thawed frozen culture, or several colonies from a selective agar plate culture, and incubated for approximately 12 hours at 37±1° C. on a shaking platform at 150 rpm (Innova 2100, New Brunswick Scientific). This seed culture was then used to inoculate a 5-L working volume fermentor containing 2×YT broth and both Ap antibiotics. The fermentor (Bioflo 3000, New Brunswick Scientific) was operated at 37±1° C., 0.2–0.4 VVM air sparge, 250 rpm in Rushton impellers. The pH was not controlled in either the flask seed culture or the fermentor. During fermentation, the pH ranged 6.5 to 7.3 in the fermentor. IPTG (1.0 M stock, prepared in sterile water) was added to the fermentor when the culture reached mid-log of growth (~0.7 O.D.600 units). Cells were induced for 2–4 hours then harvested by centrifugation using either a 28RS Heraeus (Sepatech) or RC5C superspeed centrifuge (Sorvall Instruments). Cell paste was stored at −20 C until processed.

Chemicals and Materials

Imidazole and Triton X-100 were purchased from Merck. Guanidine hydrochloride was from Fluka. Aprotinin was obtained from Sigma Chemical Company. Urea and AEBSF were from ICN-Biochemicals. All other chemicals were reagent grade or better.

Ni-NTA Superflow resin and Penta-His Antibody, BSA free were obtained from QiaGen. MicroBCA assay was obtained from Pierce; Amicon 3 filters from Millipore.

Dialysis membrane (MWCO12-14000) were from MFPI, USA. Molecular mass marker (BenchMark ladder) was from Life-technologies.

Example 4

Purification of Recombinant BASB109 from *E. coli* Extraction Purification

Cell paste from 1000 ml IPTG induced culture (~4 hours, OD620=0.5) was resuspended in 40 ml of phosphate buffer pH 7.5 containing 1 mM AEBSF and 1 mM Aprotinin as protease inhibitors. Cells were lysed in a cell disruptor. Lysate was centrifuged at 27,000 g for 20 minutes. Pellet was washed once with phosphate buffer pH 7.5 and centrifuged again at 27,000 g for 20 minutes. Pellet was suspended in 40 ml 100 mM NaH2PO4, 10 mM Tris-HCl buffer pH 8 containing 6M Guanidium Chloride (buffer A) and left for 1 hour at room temperature. Total extract was centrifuged at 27,000 g for 20 minutes. Supernatant was incubated for 1 hour at room temperature with Ni-NTA superflow resin equilibrated in buffer A. Resin was washed twice with 100 mM NaH2PO4, 10 mM Tris-HCl buffer pH 6.3, containing 8M Urea (buffer B). Elution was performed with 4×1.5 ml 100 mM NaH2PO4, 10 mM Tris-HCl buffer pH 5.9, containing 8M Urea (buffer C) followed by 4×1.5 ml 100 mM NaH2PO4, 10 mM Tris-HCl buffer pH 4.5 containing 8M Urea (buffer D). Fractions were neutralised with 25% volume of 200 mM phosphate buffer pH 7.5. Fractions containing BASB109 protein were pooled and dialyzed against 100 mM NaH2PO4 buffer pH 7.4 containing 8M Urea, then 4M Urea, then 2M Urea and finally three times against PBS buffer pH 7.4 containing 0.1% Triton-X100.

Purified BASB109 protein was quantified using Micro BCA assay reagent.

4.5 mg of purified protein were obtained, at a final concentration of 150 μg/ml.

As shown in FIG. 3-A, purified BASB109 protein appeared in SDS-PAGE analysis as a major band migrating at around 65 kDa (estimated relative molecular mass). Purity was estimated to above 90%. BASB109 protein was reactive against a mouse monoclonal antibody raised against the 6-Histidine motif (FIG. 3-B).

Example 5

Immunological Characterization: Surface Exposure of BASB109

Anti-BASB109 protein titres are determined by an ELISA using formalin-killed whole cells of *Moraxella catarrhalis*. The titre is defined as mid-point titers calculated by 4-parameter logistic model using the XL Fit software.

The titre observed with the rabbit or mouse immune sera demonstrates that the BASB109 protein is present at the surface of *M. catarrhalis* cells.

Example 6

Immunological Characterisation: Western Blot Analysis

Several strains of *M. catarrhalis* including ATCC 43617, as well as clinical isolates from various geographic regions, are grown on Muller Hinton agar plates for 24 hours at 36° C. Several colonies are used to inoculate broth. Cultures are grown until the A620 is approximately 0.6 and cells are collected by centrifugation. Cells are then concentrated and solubilized in PAGE sample buffer. The solubilized cells are then resolved on 4–20% polyacrylamide gels and the separated proteins are electrophoretically transferred to PVDF membranes. The PVDF membranes are then pretreated with saturation buffer. All subsequent incubations are carried out using this pretreatment buffer.

PVDF membranes are incubated with preimmune serum or rabbit or mouse immune seru. PVDF membranes are then washed.

PVDF membranes are incubated with biotin-labeled sheep anti-rabbit or mouse Ig. PVDF membranes are then washed 3 times with wash buffer, and incubated with streptavidin-peroxydase. PVDF membranes are then washed 3 times with wash buffer and developed with 4-chloro-1-naphtol.

Detection of a protein corresponding to BASB109 expected molecular weight that is reactive with the antisera is used to demonstrate that this protein is produced by and conserved in all Moraxella strains tested.

Example 7

Immunological Characterization: Bactericidal Activity

Complement-mediated cytotoxic activity of anti-BASB109 antibodies is examined to determine the vaccine potential of BASB109 protein antiserum that is prepared as described above. The activities of the pre-immune serum and the anti-BASB109 antiserum in mediating complement killing of *M. catarrhalis* are examined.

Strains of *M. catarrhalis* are grown on plates. Several colonies are added to liquid medium. Cultures are grown and collected until the A620 is approximately 0.4. After one wash step, the pellet is suspended and diluted.

Preimmune sera and the anti-BASB109 sera is deposited into the first well of a 96-wells plate and serial dilutions are deposited in the other wells of the same line. Live diluted *M. catarrahlis* is subsequently added and the mixture is incubated. Complement is added into each well at a working dilution defined beforehand in a toxicity assay.

Each test includes a complement control (wells without serum containing active or inactivated complement source), a positive control (wells containing serum with a know titer of bactericidal antibodies), a culture control (wells without serum and complement) and a serum control (wells without complement).

Bactericidal activity of rabbit or mice antiserum (50% killing of homologous strain) is measured.

Example 8

Presence of Antibody to BASB109 in Human Convalescent Sera

Western blot analysis of purified recombinant BASB109 is performed as described in Example 6 above, except that a pool of human sera from children infected by *M. catarrhalis* is used as the first antibody preparation. This is used to show that antisera from naturally infected individuals react to the purified recombinant protein.

Example 9

Efficacy of BASB109 Vaccine: Enhancement of Lung Clearance of *M. catarrhalis* in Mice This mouse model is based on the analysis of the lung invasion by *M. catarrhalis* following a standard intranasal challenge to vaccinated mice.

Groups of mice are immunized with BASB109 vaccine. After the booster, the mice are challenged by instillation of bacterial suspension into the nostril under anaesthesia. Mice are killed between 30 minutes and 24 hours after challenge and the lungs are removed aseptically and homogenized individually. The log10 weighted mean number of CFU/lung is determined by counting the colonies grown on agar plates after plating of dilutions of the homogenate. The arithmetic mean of the log10 weighted mean number of CFU/lung and the standard deviations are calculated for each group.

Results are analysed statistically.

In this experiment groups of mice are immunized either with BASB109 or with a killed whole cells (kwc) preparation of *M. catarrhalis* or sham immunized.

This is used to show that the kwc preparation and the BASB109 vaccine induce significant lung clearance as compared to the control group.

Example 10

Inhibition of *M. catarrhalis* Adhesion onto Cells by anti-BASB109 Antiserum This assay measures the capacity of anti BASB109 sera to inhibit the adhesion of Moraxella bacteria to epithelial cells. This activity could prevent colonization of the nasopharynx by Moraxella.

One volume of bacteria is incubated on ice with one volume of pre-immune or anti-BASB109 immune serum dilution. This mixture is subsequently added in the wells of a 24 well plate containing a confluent cells culture that is washed once with culture medium to remove traces of antibiotic. The plate is centrifuged and incubated.

Each well is then gently washed. After the last wash, sodium glycocholate is added to the wells. After incubation, the cell layer is scraped and homogenised. Dilutions of the homogenate are plated on agar plates and incubated. The number of colonies on each plate is counted and the number of bacteria present in each well calculated.

This is used to show that bacteria incubated with anti-BASB109 antiserum are inhibited in their adherence capacity to the Hep-2 cells.

Deposited Materials

A deposit containing a *Moraxella catarrhalis* Catlin strain has been deposited with the American Type Culture Collection (herein "ATCC") on Jun. 21, 1997 and assigned deposit number 43617. The deposit was described as *Branhamella catarrhalis* (Frosch and Kolle) and is a freeze-dried, 1.5–2.9 kb insert library constructed from *M. catarrhalis* isolate obtained from a transtracheal aspirate of a coal miner with chronic bronchitis. The deposit is described in Antimicrob. Agents Chemother. 21: 506–508 (1982).

The *Moraxella catarrhalis* strain deposit is referred to herein as "the deposited strain" or as "the DNA of the deposited strain."

The deposited strain contains a full length BASB109 gene.

A deposit of the vector pMC-D15 consisting of *Moraxella catarrhalis* DNA inserted in pQE30 has been deposited with the American Type Culture Collection (ATCC) on Feb. 12 1999 and assigned deposit number 207105.

The sequence of the polynucleotides contained in the deposited strain/clone, as well as the amino acid sequence of any polypeptide encoded thereby, are controlling in the event of any conflict with any description of sequences herein.

The deposit of the deposited strains have been made under the terms of the Budapest Treaty on the International Recognition of the Deposit of Micro-organisms for Purposes of Patent Procedure. The deposited strains will be irrevocably and without restriction or condition released to the public upon the issuance of a patent. The deposited strains arc provided merely as convenience to those of skill in the art and are not an admission that a deposit is required for enablement, such as that required under 35 U.S.C. §112.

SEQUENCE INFORMATION

BASB109 Polynucleotide and Polypeptide Sequences

SEQ ID NO:1

*Moraxella catarrhalis* BASB109 polynucleotide sequence from strain ATCC43617

ATGTCTAAGCCTACTTTGATAAAAACAACCTTAATTTGTGCCTTAAGTGCATTGA

TGCTCAGTGGTTGTAGCAATCAAGC

GGACAAAGCCGCCCAGCCAAAAAGCAGCACGGTAGACGCTGCCGCCAAGACAG

CAAATGCAGATAATGCTGCCTCACAAG

AACATCAAGGCGAGCTGCCTGTCATTGATGCCATTGTTACGCATGCACCAGAAGT

TCCACCACCTGTTGACCGTGACCAC

CCCGCCAAAGTGGTGGTAAAAATGGAAACCGTTGAAAAAGTCATGCGTCTGGCA

GATGGCGTGGAATATCAGTTTTGGAC

ATTTGGCGGTCAAGTTCCAGGGCAGATGATTCGTGTGCGTGAAGGCGACACCATC

GAAGTGCAGTTCTCAAACCACCCAG

ATTCAAAAATGCCCCATAATGTTGACTTTCACGCTGCCACAGGGCCTGGCGGCGG

GGCAGAAGCGTCATTTACCGCACCG

GGTCATACATCAACCTTTAGTTTTAAAGCCTTACAGCCTGGTTTGTATGTCTATCA

-continued

CTGTGCGGTTGCCCCTGTTGGCAT

GCACATTGCTAATGGCATGTATGGTTTGATTTTGGTTGAACCAAAAGAGGGCTTG

CCAAAAGTAGATAAAGAATACTATG

TCATGCAAGGCGACTTTTATACCAAAGGCAAATATGGCGAACAAGGTCTACAGC

CCTTTGATATGGAAAAAGCCATTCGA

GAAGATGCTGAATATGTTGTCTTTAATGGTTCGGTGGGGGCGTTGACTGGTGAAA

ATGCTCTAAAAGCCAAGGTTGGCGA

AACTGTTCGCTTATTTGTGGGTAACGGCGGCCCGAATTTGACATCATCATTCCAT

GTCATTGGTGAGATTTTTGATAAGG

TTCACTTTGAGGGTGGTAAGGGTGAAAACCACAATATCCAAACCACGCTAATCCC

AGCAGGTGGCGCTGCCATCACTGAA

TTTAAGGTGGATGTGCCGGGTGATTATGTCTTGGTTGACCATGCCATCTTCCGTGC

CTTTAACAAAGGGGCATTGGGCAT

ACTTAAGGTGGAAGGTGAAGAAAACCTCATGAGATTTATTCACACAAACAAACAGA

CGCTGTCTATCTGCCAGAGGGTGCCC

CACAAGCAATTGATACCCAAGAAGCACCCAAAACACCTGCACCTGCCAACTTAC

AAGAGCAGATTAAAGCAGGTAAGGCA

ACCTATGACTCTAACTGTGCTGCTTGTCACCAACCTGATGGTAAAGGCGTGCCCAA

ACGCTTTCCCACCGCTTGCCAACTC

TGACTATCTGAACGCCGACCACGCTCGTGCCGCCAGCATCGTGGCAAATGGATTG

TCTGGTAAGATTACCGTCAATGGCA

ACCAATATGAAAGCGTCATGCCTGCGATTGCTCTGAGCGACCAACAGATTGCCA

ATGTCATCACCTACACGCTTAACAGC

TTGGTAACAAAGGCGGTCAACTCAGTGCAGACGATGTGGCAAAAGCCAAAAAA

ACCAAGCCAAACTGA

SEQ ID NO:2

*Moraxella catarrhalis* BASB109 polypeptide sequence deduced from the polynucleotide of SEQ ID NO:1

MSKPTLIKTTLICALSALMLSGCSNQADKAAQPKSSTVDAAAKTANADNAASQEHQ

GELPVIDAIVTHAPE

VPPPVDRDHPAKVVVKMETVEKVMRLADGVEYQFWTFGGQVPGQMIRVREGDTIE

VQFSNHPDSKMPHNVD

FHAATGPGGGAEASFTAPGHTSTFSFKALQPGLYVYHCAVAPVGMHIANGMYGLIL

VEPKEGLPKVDKEYY

VMQGDFYTKGKYGEQGLQPFDMEKAIREDAEYVVFNGSVGALTGENALKAKVGET

VRLFVGNGGPNLTSSF

HVIGEIFDKVHFEGGKGENHNIQTTLIPAGGAAITEFKVDVPGDYVLVDHAIFRAFNK

GALGILKVEGEEN

HEIYSHKQTDAVYLPEGAPQAIDTQEAPKTPAPANLQEQIKAGKATYDSNCAACHQP

DGKGVPNAFPPLAN

SDYLNADHARAASIVANGLSGKITVNGNQYESVMPAIALSDQQIANVITYTLNSFGNK

-continued

GGQLSADDVAKAK

KTKPN

SEQ ID NO:3

*Moraxella catarrhalis* BASB109 polynucleotide sequence from strain ATCC43617

ATGTCTAAGCCTACTTTGATAAAAACAACCTTAATTTGTGCCTTAAGTGCATTGA

TGCTCAGTGGTTGTAGCAATCAAGC

GGACAAAGCCGCCCAGCCAAAAAGCAGCACGGTAGACGCTGCCGCCAAGACAG

CAAATGCAGATAATGCTGCCTCACAAG

AACATCAAGGCGAGCTGCCTGTCATTGATGCCATTGTTACGCATGCACCAGAAGT

TCCACCACCTGTTGACCGTGACCAC

CCCGCCAAAGTGGTGGTAAAAATGGAAACCGTTGAAAAAGTCATGCGTCTGGCA

GATGGCGTGGAATATCAGTTTTGGAC

ATTGGCGGTCAAGTTCCAGGGCAGATGATTCGTGTGCGTGAAGGCGACACCATC

GAAGTGCAGTTCTCAAACCACCCAG

ATTCAAAAATGCCCCATAATGTTGACTTTCACGCTGCCACAGGGCCTGGCGGCGG

GGCAGAAGCGTCATTTACCGCACCG

GGTCATACATCAACCTTTAGTTTTAAAGCCTTACAGCCTGGTTTGTATGTCTATCA

CTGTGCGGTTGCCCCTGTTGGCAT

GCACATTGCTAATGGCATGTATGGTTTGATTTTGGTTGAACCAAAAGAGGGCTTG

CCAAAAGTAGATAAAGAATACTATG

TCATGCAAGGCGACTTTTATACCAAAGGCAAATATGGCGAACAAGGTCTACAGC

CCTTTGATATGGAAAAAGCCATTCGA

GAAGATGCTGAATATGTTGTCTTTAATGGTTCGGTGGGGGCGTTGACTGGTGAAA

ATGCTCTAAAAGCCAAGGTTGGCGA

AACTGTTCGCTTATTTGTGGGTAACGGCGGCCCGAATTTGACATCATCATTCCAT

GTCATTGGTGAGATTTTTGATAAGG

TTCACTTTGAGGGTGGTAAGGGTGAAAACCACAATATCCAAACCACGCTAATCCC

AGCAGGTGGCGCTGCCATCACTGAA

TTTAAGGTGGATGTGCCGGGTGATTATGTCTTGGTTGACCATGCCATCTTCCGTGC

CTTTAACAAAGGGGCATTGGGCAT

ACTTAAGGTGGAAGGTGAAGAAAATCATGAGATTTATTCACACAAACAAACAGA

CGCTGTCTATCTGCCAGAGGGTGCCC

CACAAGCAATTGATACCCAAGAAGCACCCAAAACACCTGCACCTGCCAACTTAC

AAGAGCAGATTAAAGCAGGTAAGGCA

ACCTATGACTCTAACTGTGCTGCTTGTCACCAACCTGATGGTAAAGGCGTGCCAA

ACGCTTTCCCACCGCTTGCCAACTC

TGACTATCTGAACGCCGACCACGCTCGTGCCGCCAGCATCGTGGCAAATGGATTG

TCTGGTAAGATTACCGTCAATGGCA

ACCAATATGAAAGCGTCATGCCTGCGATTGCTCTGAGCGACCAACAGATTGCCA

ATGTCATCACCTACACGCTTAACAGC

-continued

TTTGGTAACAAAGGCGGTCAACTCAGTGCAGACGATGTGGCAAAAGCCAAAAAA

ACCAAGCCAAAC

SEQ ID NO:4

*Moraxella catarrhalis* BASB109 polypeptide sequence deduced from the polynucleotide of SEQ ID NO:3

MSKPTLIKTTLICALSALMLSGCSNQADKAAQPKSSTVDAAAKTANADNAASQEHQ

GELPVIDAIVTHAPE

VPPPVDRDHPAKVVVKMETVEKVMRLADGVEYQFWTFGGQVPGQMIRVREGDTIE

VQFSNHPDSKMPHNVD

FHAATGPGGGAEASFTAPGHTSTFSFKALQPGLYVYHCAVAPVGMHIANGMYGLIL

VEPKEGLPKVDKEYY

VMQGDFYTKGKYGEQGLQPFDMEKAIREDAEYVVFNGSVGALTGENALKAKVGET

VRLFVGNGGPNLTSSF

HVIGEIFDKVHFEGGKGENHNIQTTLIPAGGAAITEFKVDVPGDYVLVDHAIFRAFNK

GALGILKVEGEEN

HEIYSHKQTDAVYLPEGAPQAIDTQEAPKTPAPANLQEQIKAGKATYDSNCAACHQP

DGKGVPNAFPPLAN

SDYLNADHARAASIVANGLSGKITVNGNQYESVMPAIALSDQQIANVITYTLNSFGNK

GGQLSADDVAKAK

KTKPN

SEQ ID NO:5

AAG CGA ACA GTT TCG CCA ACC

SEQ ID NO:6

GGG GGC GTT GAC TGG TGA AAA TG

SEQ ID NO:7

GTA AAA CGA CGG CCA GT

SEQ ID NO:8

CAG GAA ACA GCT ATG AC

SEQ ID NO:9

ACA TGT CTA AGC CTA CTT TGA T

SEQ ID NO:10

AGA TCT GTT TGG CTT GGT TTT TTT GGC

---

What is claimed is:

1. An isolated, recombinant polypeptide comprising a member selected from the group consisting of (a) the amino acid sequence SEQ ID NO:2 and (b) an immunogenic fragment of at least 15 contiguous amino acids of SEQ ID NO:2, wherein the immunogenic fragment, when administered to a subject in a suitable composition which can include an adjuvant, or a suitable carrier coupled to the polypeptide, induces an antibody or T-cell mediated immune response that recognizes the polypeptide SEQ ID NO:2; wherein the immunogenic fragment is selected from one of the following contiguous segments of SEQ ID NO:2;

1–15; 2–16; 3–17; 4–18; 5–19; 6–20; 7–21; 8–22; 9–23; 10–24; 11–25; 12–26; 13–27; 14–28; 15–29; 16–30; 17–31; 18–32; 19–33; 20–34; 21–35; 22–36; 23–37; 24–38; 25–39; 26–40; 27–41; 28–42; 29–43; 30–44; 31–45; 32–46; 33–47; 34–48; 45–49; 46–50; 37–51; 38–52; 39–53; 40–54; 41–55; 42–56; 43–57; 44–58; 45–59; 46–60; 47–61; 48–62; 49–63; 50–64; 51–65; 52–66; 53–67; 54–68; 55–69; 56–70; 57–71; 58–72; 59–73; 60–74; 61–75; 62–76; 63–77; 64–78; 65–79; 66–80; 67–81; 68–82; 69–83; 70–84; 71–85; 72–86; 73–87; 74–88; 75–89; 76–90; 77–91; 78–92; 79–93; 80–94; 81–95; 82–96; 83–97; 84–98; 85–99; 86–100; 87–101; 88–102; 89–103; 90–104; 91–105; 92–106; 93–107; 94–108; 95–109; 96–110; 97–111; 98–112; 99–113; 100–114; 101–115; 102–116; 103–117; 104–118; 105–119; 106–120; 107–121; 108–122; 109–123; 110–124; 111–125; 112–126; 113–127; 114–128; 115–129; 116–130; 117–131; 118–132; 119–133; 120–134; 121–135; 122–136; 123–137; 124–138; 125–139; 126–140; 127–141; 128–142; 129–143; 130–144; 131–145; 132–146; 133–147; 134–148; 135–149; 136–150; 137–151; 138–152; 139–153; 140–154; 141–155; 142–156; 143–157; 144–158; 145–159; 146–160; 147–161; 148–162; 149–163; 150–164; 151–165; 152–166; 153–167; 154–168; 155–169; 156–170; 157–171; 158–172; 159–173; 160–174; 161–175; 162–176; 163–177; 164–178; 165–179; 166–180; 167–181; 168–182; 169–183; 170–184; 171–185; 172–186; 173–187; 174–188; 175–189; 176–190; 177–191; 198–212; 199–213; 200–214; 201–215; 202–216; 203–217; 204–218; 205–219; 206–220; 207–221; 208–222; 209–223; 210–224; 211–225; 212–226; 213–227; 214–228; 215–229; 216–230; 217–231; 218–232; 219–233; 220–234; 221–235; 222–236; 223–237; 224–238; 225–239; 226–240; 227–241; 228–242; 229–243; 230–244; 231–245; 232–246; 233–247; 234–248; 235–249; 236–240; 237–241; 238–252; 239–253; 240–254; 241–255; 242–256; 243–257; 244–258; 245–259; 246–260; 247–261; 248–262; 249–263; 250–264; 251–265; 252–266; 253–267; 254–268; 255–269; 256–270; 257–271; 258–272; 259–273; 260–274; 261–275; 262–276; 263–277; 264–278; 265–279; 266–280; 267–281; 268–282; 269–283; 270–284; 271–285; 272–286; 273–287; 274–288; 275–289; 276–290; 277–291; 278–292; 279–293; 280–294; 281–295; 282–296; 283–297; 284–298; 285–299; 286–300; 287–301; 288–302; 289–303; 290–304; 291–305; 292–306; 293–307; 294–308; 295–309; 296–310; 297–311; 298–312; 299–313; 300–314; 301–315; 302–316; 303–317; 304–318; 305–319; 306–320; 307–321; 308–322; 309–323; 310–324; 311–325; 312–326; 313–327; 314–328; 315–329; 316–330; 317–331; 318–332; 319–333; 320–334; 321–335; 322–336; 323–337; 324–338; 325–339; 326–340; 327–341; 328–342; 329–343; 330–344; 331–345; 332–346; 333–347; 334–348; 335–349; 336–350; 337–351; 338–352; 339–353; 340–354; 341–355; 342–356; 343–357; 344–358; 345–359; 346–360; 347–361; 348–362; 349–363; 350–364; 351–365; 352–366; 353–367; 354–368; 355–369; 356–370; 357–371; 358–372; 359–373; 360–374; 361–375; 362–376; 363–377; 364–378; 365–379; 366–380; 367–381; 368–382; 369–383; 370–384; 371–385; 372–386; 373–387; 374–388; 375–389; 376–390; 377–391; 378–392; 379–393; 380–394; 381–395; 382–396; 383–397; 384–398; 385–399; 386–400; 387–401; 388–402; 389–403; 390–404; 391–405; 392–406; 393–407; 394–408; 395–409; 396–410; 397–411; 398–412; 399–413; 400–414; 401–415; 402–416; 403–417; 404–418; 405–419; 406–420; 407–421; 408–422; 409–423; 410–424; 411–425; 412–426; 413–427; 414–428; 415–429; 416–430; 417–431; 418–432; 419–433; 420–434; 421–435; 422–436; 423–437; 424–438; 425–439; 426–440; 427–441; 428–442; 429–443; 430–444; 431–445; 432–446; 433–447; 434–448; 435–449; 436–450; 437–451; 438–452; 439–453; 440–454; 441–455; 442–456; 443–457; 444–458; 445–459; 446–460; 447–461; 448–462; 449–463; 450–464; 451–465; 452–466; 453–467; 454–468; 455–469; 456–470; 457–471; 458–472; 459–473; 460–474; 461–475; 462–476; 463–477; 464–478; 465–479; 466–480; 467–481; 468–482; 469–483; 470–484; 471–485; 472–486; 473–487; 474–488; 475–489; 476–490; 477–491; 478–492; 479–493; 480–494; 481–495; 482–496; 483–497; 484–498; 485–499; 486–500; 487–501; and 488–502.

2. The isolated recombinant polypeptide of claim 1, wherein the polypeptide is according to (a).

3. The isolated, recombinant polypeptide of claim 1, wherein the polypeptide is according to (b).

4. The isolated, recombinant polypeptide of claim 1, wherein the immunogenic fragment of (b) comprises at least 20 contiguous amino acids of SEQ ID NO:2, wherein the immunogenic fragment, when administered to a subject in a suitable composition which can include an adjuvant, or a suitable carrier coupled to the polypeptide, induces an antibody or T-cell mediated immune response that recognizes the polypeptide SEQ ID NO:2; wherein the immunogenic fragment is selected from one of the following contiguous segments of SEQ ID NO:2;

1–20; 2–21; 3–22; 4–23; 5–24; 6–25; 7–26; 8–27; 9–28; 10–29; 11–30; 12–31; 13–32; 14–33; 15–34; 16–35; 17–36; 18–37; 19–38; 20–39; 21–40; 22–41; 23–42; 24–43; 25–44; 26–45; 27–46; 28–47; 29–48; 30–49; 31–50; 32–51; 33–52; 34–53; 35–54; 36–55; 37–56; 38–57; 39–58; 40–59; 41–60; 42–61; 43–62; 44–63; 45–64; 46–65; 47–66; 48–67; 49–68; 50–69; 51–70; 52–71; 53–72; 54–73; 55–74; 56–75; 57–76; 58–77; 59–78; 60–79; 61–80; 62–81; 63–82; 64–83; 65–84; 66–85; 67–86; 68–87; 69–88; 70–89; 71–90; 72–91; 73–92; 74–93; 75–94; 76–95; 77–96; 78–97; 79–98; 80–99; 81–100; 82–101; 83–102; 84–103; 85–104; 86–105; 87–106; 88–107; 89–108; 90–109; 91–110; 92–111; 93–112; 94–113; 95–114; 96–115; 97–116; 98–117; 99–118; 100–119; 101–120; 102–121; 103–122; 104–123; 105–124; 106–125; 107–126; 108–127; 109–128; 110–129; 111–130; 112–131; 113–132; 114–133; 115–134; 116–135; 117–136; 118–137; 119–138; 120–139; 121–140; 122–141;

123–142; 124–143; 125–144; 126–145; 127–146; 128–147; 129–148; 130–149; 131–150; 132–151; 133–152; 134–153; 135–154; 136–155; 137–156; 138–157; 139–158; 140–159; 141–160; 142–161; 143–162; 144–163; 145–164; 146–165; 147–166; 148–167; 149–168; 150–169; 151–170; 152–171; 153–172; 154–173; 155–174; 156–175; 157–176; 158–177; 159–178; 160–179; 161–180; 162–181; 163–182; 164–183; 165–184; 166–185; 167–186; 168–187; 169–188; 170–189; 171–190; 172–191; 198–217; 199–218; 200–219; 201–220; 202–221; 203–222; 204–223; 205–224; 206–225; 207–226; 208–227; 209–228; 210–229; 211–230; 212–231; 213–232; 214–233; 215–234; 216–235; 217–236; 218–237; 219–238; 220–239; 221–240; 222–241; 223–242; 224–243; 225–244; 226–245; 227–246; 228–247; 229–248; 230–249; 231–250; 232–251; 233–252; 234–253; 235–254; 236–255; 237–256; 238–257; 239–258; 240–259; 241–260; 242–261; 243–262; 244–263; 245–264; 246–265; 247–266; 248–267; 249–268; 250–269; 251–270; 252–271; 253–272; 254–273; 255–274; 256–275; 257–276; 258–277; 259–278; 260–279; 261–280; 262–281; 263–282; 264–283; 265–284; 266–285; 267–286; 268–287; 269–288; 270–289; 271–290; 272–291; 273–292; 274–293; 275–294; 276–295; 277–296; 278–297; 279–298; 280–299; 281–300; 282–301; 283–302; 284–303; 285–304; 286–305; 287–306; 288–307; 289–308; 290–309; 291–310; 292–311; 293–312; 294–313; 295–314; 296–315; 297–316; 298–317; 299–318; 300–319; 301–320; 302–321; 303–322; 304–323; 305–324; 306–325; 307–326; 308–327; 309–328; 310–329; 311–330; 312–331; 313–332; 314–333; 315–334; 316–335; 317–336; 318–337; 319–338; 320–339; 321–340; 322–341; 323–342; 324–343; 325–344; 326–345; 327–346; 328–347; 329–348; 330–349; 331–350; 332–351; 333–352; 334–353; 335–354; 336–355; 337–356; 338–357; 339–358; 340–359; 341–360; 342–361; 343–362; 344–363; 345–364; 346–365; 347–366; 348–367; 349–368; 350–369; 351–370; 352–371; 353–372; 354–373; 355–374; 356–375; 357–376; 358–377; 359–378; 360–379; 361–380; 362–381; 363–382; 364–383; 365–384; 366–385; 367–386; 368–387; 369–388; 370–389; 371–390; 372–391; 373–392; 374–393; 375–394; 376–395; 377–396; 378–397; 379–398; 380–399; 381–400; 382–401; 383–402; 384–403; 385–404; 386–405; 387–406; 388–407; 389–408; 390–409; 391–410; 392–411; 393–412; 394–413; 395–414; 396–415; 397–416; 398–417; 399–418; 400–419; 401–420; 402–421; 403–422; 404–423; 405–424; 406–425; 407–426; 408–427; 409–428; 410–429; 411–430; 412–431; 413–432; 414–433; 415–434; 416–435; 417–436; 418–437; 419–438; 420–439; 421–440; 422–441; 423–442; 424–443; 425–444; 426–445; 427–446; 428–447; 429–448; 430–449; 431–450; 432–451; 433–452; 434–453; 435–454; 436–455; 437–456; 438–457; 439–458; 440–459; 441–460; 442–461; 443–462; 444–463; 445–464; 446–465; 447–466; 448–467; 449–468; 450–469; 451–470; 452–471; 453–472; 454–473; 455–474; 456–475; 457–476; 458–477; 459–478; 460–479; 461–480; 462–481; 463–482; 464–483; 465–484; 466–485; 467–486; 468–487; 469–488; 470–489; 471–490; 472–491; 473–492; 474–493; 475–494; 476–495; 477–496; 478–497; 479–498; 480–499; 481–500; 482–501; and 483–502.

5. The isolated, recombinant polypeptide of claim 1, wherein the isolated, recombinant polypeptide consists of SEQ ID NO:2.

6. A fusion protein comprising the isolated, recombinant polypeptide of claim 1.

7. An immunogenic composition comprising the isolated, recombinant polypeptide of claim 1 and a pharmaceutically acceptable carrier.

8. The immunogenic composition of claim 7, wherein the immunogenic composition comprises at least one other *Moraxella catarrhalis* antigen.

9. A method for inducing an immune response in a mammal comprising administration of the polypeptide of claim 1.

10. A fusion protein comprising the isolated, recombinant polypeptide of claim 2.

11. An immunogenic composition comprising the isolated, recombinant polypeptide of claim 2.

12. A fusion protein comprising the isolated, recombinant polypeptide of claim 3.

13. An immunogenic composition comprising the isolated, recombinant polypeptide of claim 3.

* * * * *